(12) United States Patent
Goldfine et al.

(10) Patent No.: US 8,494,810 B2
(45) Date of Patent: Jul. 23, 2013

(54) COMPONENT ADAPTIVE LIFE MANAGEMENT

(75) Inventors: Neil J. Goldfine, Newton, MA (US);
Yanko K. Sheiretov, Waltham, MA (US); Andrew P. Washabaugh, Chula Vista, CA (US); Vladimir A. Zilberstein, Chestnut Hill, MA (US); David C. Grundy, Chelmsford, MA (US); Robert J. Lyons, Bostn, MA (US); David A. Jablonski, Whitman, MA (US); Floyd W. Spencer, Albuquerque, NM (US)

(73) Assignee: Jentek Sensors, Inc., Waltham, MA (US)

( * ) Notice: Subject to any disclaimer, the term of this patent is extended or adjusted under 35 U.S.C. 154(b) by 292 days.

(21) Appl. No.: 12/795,538

(22) Filed: Jun. 7, 2010

(65) Prior Publication Data

US 2011/0060568 A1    Mar. 10, 2011

Related U.S. Application Data

(60) Provisional application No. 61/184,672, filed on Jun. 5, 2009.

(51) Int. Cl.
*G06F 19/00* (2011.01)
(52) U.S. Cl.
USPC .......................................................... 702/183
(58) Field of Classification Search
USPC ............... 702/183, 34; 703/2, 6; 73/602, 799; 324/225, 228
See application file for complete search history.

(56) References Cited

U.S. PATENT DOCUMENTS

| 4,175,447 | A | 11/1979 | Fukuhara |
| 4,574,642 | A | 3/1986 | Fleischman |
| 5,047,719 | A | 9/1991 | Johnson et al. |
| 5,262,722 | A | 11/1993 | Hedengren et al. |

(Continued)

OTHER PUBLICATIONS

Mohanty, et al., "Off-Line and On-Line Fatigue Crack Growth Prediction Using Multivariate Gaussian Process," Submitted to AIAA Journal in 2008, 24 pages.

(Continued)

*Primary Examiner* — Bryan Bui
(74) *Attorney, Agent, or Firm* — Hamilton, Brook, Smith & Reynolds, P.C.

(57) ABSTRACT

A framework for adaptively managing the life of components. A sensor provides non-destructive test data obtained from inspecting a component. The inspection data may be filtered using reference signatures and by subtracting a baseline. The filtered inspection data and other inspection data for the component is analyzed to locate flaws and estimate the current condition of the component. The current condition may then be used to predict the component's condition at a future time or to predict a future time at which the component's condition will have deteriorated to a certain level. A current condition may be input to a precomputed database to look up the future condition or time. The future condition or time is described by a probability distribution which may be used to assess the risk of component failure. The assessed risk may be used to determine whether the part should continue in service, be replaced or repaired. A hyperlattice database is used with a rapid searching method to estimate at least one material condition and one usage parameter, such as stress level for the component. The hyperlattice is also used to rapidly predict future condition, associated uncertainty and risk of failure.

23 Claims, 28 Drawing Sheets

U.S. PATENT DOCUMENTS

| | | | |
|---|---|---|---|
| 5,278,498 | A | 1/1994 | Vernon et al. |
| 5,315,234 | A | 5/1994 | Sutton, Jr. et al. |
| 5,371,462 | A | 12/1994 | Hedengren et al. |
| 5,453,689 | A | 9/1995 | Goldfine et al. |
| 5,793,206 | A | 8/1998 | Goldfine et al. |
| 5,966,011 | A | 10/1999 | Goldfine et al. |
| 6,144,206 | A | 11/2000 | Goldfine et al. |
| 6,188,218 | B1 | 2/2001 | Goldfine et al. |
| 6,198,279 | B1 | 3/2001 | Goldfine et al. |
| 6,226,597 | B1 | 5/2001 | Eastman et al. |
| 6,351,120 | B2 | 2/2002 | Goldfine |
| 6,377,039 | B1 | 4/2002 | Goldfine et al. |
| 6,380,747 | B1 | 4/2002 | Goldfine et al. |
| 6,420,867 | B1 | 7/2002 | Goldfine et al. |
| 6,486,673 | B1 | 11/2002 | Goldfine et al. |
| 6,636,813 | B1 | 10/2003 | Isobe et al. |
| 6,657,429 | B1 | 12/2003 | Goldfine et al. |
| 6,727,691 | B2 | 4/2004 | Goldfine et al. |
| 6,781,387 | B2 | 8/2004 | Goldfine et al. |
| 6,784,662 | B2 | 8/2004 | Schlicker et al. |
| 6,798,198 | B2 | 9/2004 | Tsukernik et al. |
| 6,952,095 | B1 | 10/2005 | Goldfine et al. |
| 6,992,482 | B2 | 1/2006 | Shay et al. |
| 6,995,557 | B2 | 2/2006 | Goldfine et al. |
| 7,006,947 | B2 | 2/2006 | Tryon, III et al. |
| 7,049,811 | B2 | 5/2006 | Schlicker et al. |
| RE39,206 | E | 7/2006 | Goldfine et al. |
| 7,095,224 | B2 | 8/2006 | Goldfine et al. |
| 7,106,055 | B2 | 9/2006 | Goldfine et al. |
| 7,107,491 | B2 | 9/2006 | Graichen et al. |
| 7,161,350 | B2 | 1/2007 | Goldfine et al. |
| 7,161,351 | B2 | 1/2007 | Goldfine et al. |
| 7,183,764 | B2 | 2/2007 | Goldfine et al. |
| 7,188,532 | B2 | 3/2007 | Goldfine et al. |
| 7,230,421 | B2 | 6/2007 | Goldfine et al. |
| 7,280,940 | B2 | 10/2007 | Goldfine et al. |
| 7,348,771 | B2 | 3/2008 | Goldfine et al. |
| 7,385,392 | B2 | 6/2008 | Schlicker et al. |
| 7,411,390 | B2 | 8/2008 | Goldfine et al. |
| 7,451,639 | B2 | 11/2008 | Goldfine et al. |
| 7,451,657 | B2 | 11/2008 | Goldfine et al. |
| 7,467,057 | B2 | 12/2008 | Sheiretov et al. |
| 7,518,360 | B2 | 4/2009 | Goldfine et al. |
| 7,526,964 | B2 | 5/2009 | Goldfine et al. |
| 7,528,598 | B2 | 5/2009 | Goldfine et al. |
| 7,634,383 | B2 | 12/2009 | Engel et al. |
| 2003/0025497 | A1 | 2/2003 | Collingwood et al. |
| 2003/0154052 | A1 | 8/2003 | Samata et al. |
| 2003/0164700 | A1 | 9/2003 | Goldfine et al. |
| 2004/0167756 | A1 | 8/2004 | Yonezawa |
| 2004/0225474 | A1 | 11/2004 | Goldine et al. |
| 2004/0232911 | A1 | 11/2004 | Schlicker et al. |
| 2005/0096873 | A1 | 5/2005 | Klein |
| 2005/0146324 | A1 | 7/2005 | Goldfine et al. |
| 2006/0009923 | A1* | 1/2006 | Shay et al. ...... 702/38 |
| 2006/0265261 | A1 | 11/2006 | Wetzer et al. |
| 2007/0069720 | A1 | 3/2007 | Goldfine et al. |
| 2007/0236214 | A1 | 10/2007 | Goldfine et al. |
| 2007/0239407 | A1* | 10/2007 | Goldfine et al. ............ 703/2 |
| 2008/0177516 | A1 | 7/2008 | Vasudevan et al. |
| 2008/0289423 | A1 | 11/2008 | Gordon et al. |
| 2009/0037122 | A1 | 2/2009 | Engel et al. |
| 2010/0082267 | A1 | 4/2010 | Schimert et al. |
| 2010/0106430 | A1 | 4/2010 | Balestra |

OTHER PUBLICATIONS

U.S. non-final Office Action dated Mary 14, 2012 for U.S. Appl. No. 12/795,561.

Final Office Action dated Jul. 20, 2011, for U.S. Appl. No. 11/653,067.

Goldfine, et al., "Eddy Current Sensor Networks for Aircraft Fatigue Monitoring," ASNT Materials Evaluation, Aerospace Health Monitoring, vol. 61, No. 7, pp. 1-13 (Jul. 2003).

Zilberstein, et al., "Early Detection and Monitoring of Fatigue in High Strength Steels with MWM-Arrays," International Journal of Fatigue, vol. 27, pp. 1644-1652 (Jul. 28, 2005).

Goldfine, N., Windoloski, M., Zilberstein,V., Contag, G., N. Phan, R. Davis, "Mapping & Tracking of Damage in Titanium Components for Adaptive Life Management," $10^{th}$ Joint NASA/DoD/ FAA Conference on Aging Aircraft, Atlanta, GA; Apr. 16-20, 2007.

Goldfine, N., Grundy, D., Washabaugh, A., Zilberstein, V., Weiss, V., Davis, M., Schaff, J., Hullander, T., Davis, W., Contag, G., Timmons, A., Hardman, B., "Damage and Usage Monitoring for Vertical Flight Vehicles," American Helicopter Society (AHS) $63^{rd}$ Annual Forum and Technology Display; Virginia Beach, Virginia; May 1-3, 2007.

Goldfine, N., Sheiretov, Y., Washabaugh, A., Zilberstein, V., Jablonski, D., Contag, G., "Sensing and Risk Assessment for Condition Based Maintenance 'Plus' ", $12^{th}$ Joint FAA/DoD/NASA Conference on Aging Aircraft, Kansas City, MO. May 4-9, 2009.

Goldfine, N., Grundy, D., Jablonski, D., Zilberstein, V., "Automated Fatigue Test Monitoring and Damage Evolution Tracking for Prognosis in Support of Condition Based Maintenance Decisions —Part I: Fatigue Tests," ASM AeroMat, Dayton, OH, Jun. 7-10, 2009.

Goldfine, N., Denenberg, S., Lyons, R., Sheiretov, Y., Washabaugh, A., "Automated Fatigue Test Monitoring and Damage Evolution Tracking for Prognosis in Support of Condition Based Maintenance Decisions —Part II: Prognosis," ASM AeroMat, Dayton, OH, Jun. 7-10, 2009.

Goldfine, N., "Remaining Life Prediction for Individual Components from Sparse Data (for CBM+)," Navy Opportunity Forum, Arlington, VA, Jun. 7-10, 2009.

U.S. Office Action mailed Feb. 11, 2011 for U.S. Appl. No. 11/653,067.

Burgard, W., et al., "Estimating the Absolute Position of a Mobile Robot Using Position Probability Grids," *Proc. of the Fourteenth National Conference on Artificial Intelligence (AAAI-96)*.

Gupta, S., et al., "Statistical Pattern Analysis of Ultrasonic Signals for Fatigue Damage Detection in Mechanical Structures," *NDT&E International*, 41: 491-500 (2008).

Righiniotis, T.D., and Chryssanthopoulos, M.K., "Fatigue and Fracture Simulation of Welded Bridge Details Through a Bi-Linear Crack Growth Law," *Structural Safety*, 26: 141-158 (2004).

Rooke, D.P. And Cartwright, D.J., "Two Cracks at a Circular Hole in a Rectangular Sheet: Uniform Uniaxial Tensile Stress," *Compendium of Stress Intensity Factors*, pp. 158-159 (1976).

U.S. non-final Office Action dated Jan. 29, 2013 for U.S. Appl. No. 12/795,561.

OriginLab, "Peak Analysis Tool," Aug. 7, 2007, OriginLab, Software description; http://wayback.archive.org/web/20070807135908/ http://www.originlab.com/fileexchange/details.aspx?fid=68.

* cited by examiner

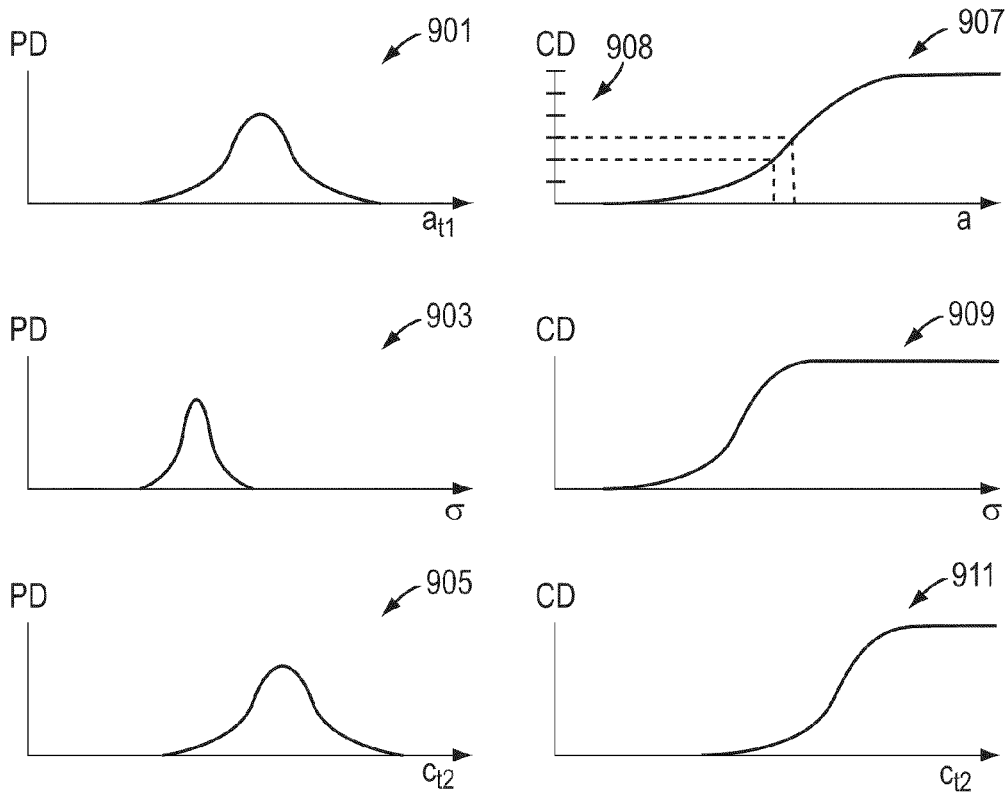
FIG. 9A
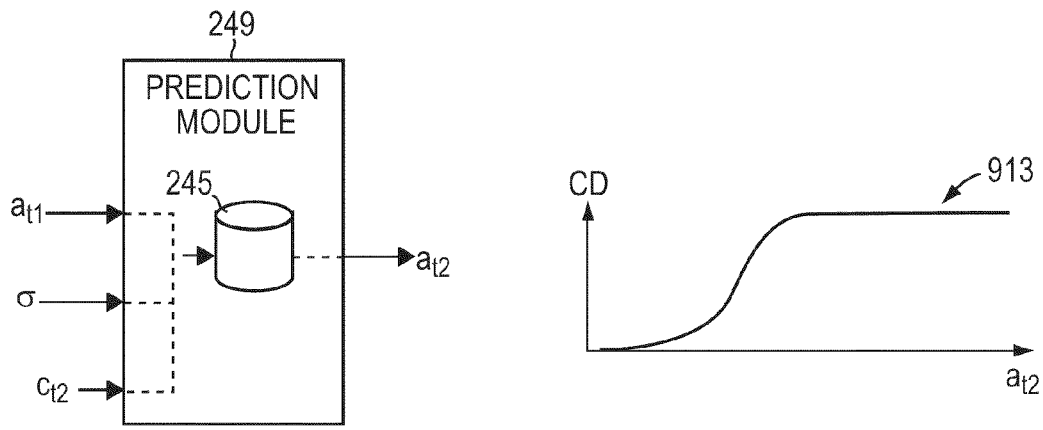
FIG. 9B
FIG. 9C

FIG. 12D

| 1205 | |
|---|---|
| Device | |
| Device Serial Number | |
| Component | |
| Component Serial Number | |
| Operator | |
| Date | |
| Time | |
| Temperature | |
| Relative Humidity | |
| NDT Instrument | |
| NDT Instrument Serial Number | |
| NDT Sensor | |
| NDT Sensor Serial Number | |
| Component Material | |
| Component Surface Treatment | |
| Previous CBM action | |

FIG. 12E

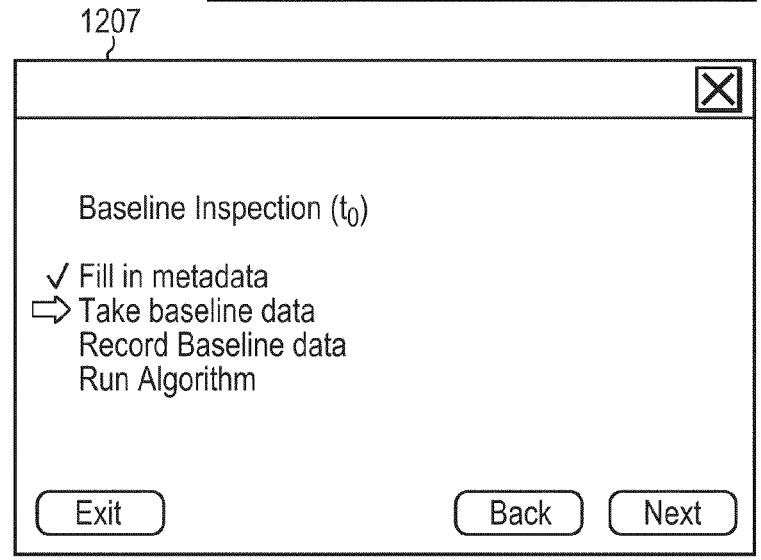

1207

Baseline Inspection ($t_0$)

✓ Fill in metadata
⇨ Take baseline data
   Record Baseline data
   Run Algorithm

[Exit]    [Back] [Next]

FIG. 12F

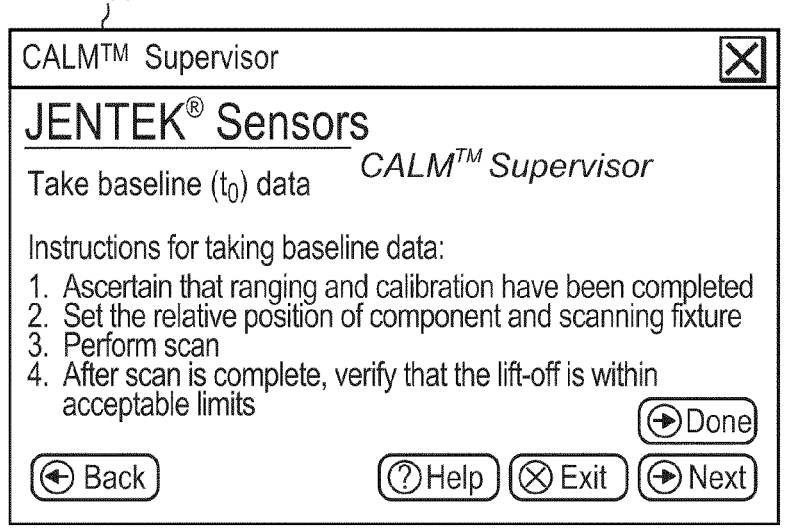

1209

CALM™ Supervisor

JENTEK® Sensors

Take baseline ($t_0$) data    *CALM™ Supervisor*

Instructions for taking baseline data:
1. Ascertain that ranging and calibration have been completed
2. Set the relative position of component and scanning fixture
3. Perform scan
4. After scan is complete, verify that the lift-off is within acceptable limits

[⊙ Done]
[⊙ Back]   [? Help] [⊗ Exit] [⊙ Next]

COMPONENT ADAPTIVE LIFE MANAGEMENT

RELATED APPLICATION

This application claims the benefit of U.S. Provisional Application No. 61/184,672, filed on Jun. 5, 2009, the entire teachings of which application are incorporated herein by reference.

BACKGROUND OF THE INVENTION

There are many applications where using a component to failure is unacceptable, and thus the component must be replaced when the risk of failure is too high. The decision of when to retire a component is a tradeoff between at least the cost of replacement and the risk of failure should the part continue to be used.

Component failure is preceded by deterioration in the condition of the component. Deterioration of a component's condition is caused by the development and growth of flaws in the component. Flaws for metals may include cracks, microcracks, inclusions, residual stress variations, microstructure variations, mechanical damage such as dents and scratches, corrosion pits, and machining effects. Flaws for composites might include fiber damage, bridging, impact damage, disbands, and delaminations. Flaws may originate during manufacture or develop once the component is in service. While in service the component may be exposed to operating conditions that lead to the development and/or further growth of the flaw. Different types of components may be more sensitive to different types of loads. Operating conditions that may affect the condition of a component may include temperature, temperature variation (e.g., freeze-thaw cycles), acceleration, vibration, voltage, pressure, rotational speed, mechanical stress, static loading, dynamic loading, impact events, and any other physical process that contributes to the development and/or growth of component flaws.

In many applications a component is in use intermittently and thus the operating conditions may not be persistent in time. Accordingly, the in-service time of a component may be measured in effective usage cycles, rather than in time directly. For example, an airplane component may be exposed to adverse operating conditions principally during each take off and landing cycles (or ground-air-ground, "GAG", cycles). The operating environment while the aircraft is grounded or cruising may have significantly less contribution to flaw growth than the operating conditions during takeoff and landing. Accordingly, a suitable in-service time unit may be takeoff/land cycles. Though, other suitable measures of in-service time may be used.

Safe life models have been used to predict the life of components. These models consider the operating conditions that cause damage to a component and estimate the intensity of these conditions while the component is in service. Assuming an initial flaw site, safe life models predict the growth of the flaw as the component is exposed to worst case operating conditions. Component failure may be defined, for example, by a point in the growth of a flaw in the component at which the component may no longer serve its intended purpose. The component may be replaced when the service time of the component reaches some fraction of the service time at which the component is predicted by the safe life models to fail (e.g. 50%).

Periodic inspection of components may also be used to detect flaws. The inspection may not only look for the presence of flaws but also to characterize the flaw with one or more features. For example, a crack in a component may be characterized by the crack's length. Component flaw growth models may then be used to predict, for example, the likelihood the flaw will lead to component failure by a future time. Plot 100, shown in FIG. 1, sketches a curve 101 representing the probability of failure within a time, $\Delta t$. A damage tolerance limit 103 is selected based on an acceptable probability of failure 105.

Because failure is probabilistic, inspections are traditionally scheduled periodically so that a flaw can be detected early in its growth cycle, well before it is likely to develop to the point of causing component failure. Different inspection technologies will be capable of detecting flaws at different points in their growth cycle and therefore the inspection interval depends upon the type of inspection being performed and its expected detection performance at the location of interest.

SUMMARY OF THE INVENTION

In accordance with an embodiment of the invention, there is provided an inspection system. The inspection system comprises a sensor for collecting first spatial data from a component, the first spatial data comprising a first sensor response for at least one location on the component; and a computing system. The computing system comprises an inspection archive comprising second spatial data having a second sensor response for the component; a database comprising a plurality of data points, each data point storing a material condition of the component and a time; a filtering module to spatially register the first spatial data and the second spatial data; an estimation module to estimate a current condition of the component based at least in part on the spatially registered first and second spatial data; and a prediction module to predict a future condition of the component, based at least in part on the current condition, using the database.

In further, related embodiments, the database may be generated offline using a phenomenological model. The data points may span a range of interest for each of the material condition and the time, and each database data point may also include values for at least two properties to be estimated, the values being generated using a model. The material condition may be crack size, the time may be measured in equivalent cycles, and one of the two values estimated at each data point may be remaining life. The current condition may be described by a probability density function, and the prediction module may generate a distribution function describing, probabilistically, the future condition of the component. The prediction module may predict the future condition of the component at a next scheduled inspection time, and the computing system may further comprise: a decision module that determines whether the future condition predicted at the next scheduled inspection time has a risk of failure that exceeds a damage tolerance limit. The decision module may determine that the risk of failure at the next scheduled inspection exceeds the damage tolerance threshold limit, and in response may provide an instruction to replace or repair the component. Further, if the decision module determines that the risk of failure at the next scheduled inspection exceeds the damage tolerance limit, then in response the decision module may reschedule the next inspection time to an earlier time.

In another embodiment according to the invention, there is provided a computer-readable storage medium comprising computer-executable instructions that, when executed by at least one processor, perform a method comprising acts of: receiving at least two sets of sensor data, each of the at least two sets of sensor data comprising spatial data for a measured material condition of a component; spatially registering the at least two sets of sensor data with respect to each other and the component; computing a change in the material condition of the component from the spatially registered at least two sets of sensor data; estimating the current condition based at least in part on the change in the material condition; and predicting a future condition of the component at a future time based at least in part on the estimated current condition.

In further, related embodiments, the at least two sets of sensor data may comprise three sets of sensor data, and the method may further comprise computing a second change, of the material condition using the three sets of sensor data, wherein predicting the future condition is further based on the second change. The future condition of the component may be predicted using a database comprising a plurality of precomputed material conditions of the component, each precomputed material condition computed for a respective operating condition and time. Predicting the future condition may comprise interpolating the future condition at the future time from the precomputed material conditions in the database. Predicting the future condition of the component may comprise determining a distribution function describing, probabilistically, the future condition of the component at the future time. The future time at which the future condition of the component is predicted may be a next scheduled inspection time. The method may further comprise determining whether the future condition predicted at the next scheduled inspection time has a probability above a threshold that said future condition may exceed a damage tolerance limit and, if so, providing an instruction to replace or repair the component or to reschedule the next inspection time to an earlier time. Predicting the future condition may comprise determining the future time as a time at which the future condition meets a replacement condition for the component. The future time may be measured in equivalent fatigue cycles. The future condition may be a predefined crack size limit. The method may further comprise an act of predicting a probability distribution for a future condition of the component using a probability distribution function for the current condition and a hyperlattice generated using a progression model for a process. The process may be crack initiation and growth; the evolution of a medical condition; a manufacturing process; a motion of a device; or a machining process.

In another embodiment according to the invention, there is provided a method for generating a hyperlattice. The method comprises acts of: obtaining calibration information, the calibration information comprising data obtained from sensor measurements; and operating a processor to perform acts of: selecting parameters for a model such that the calibration information is predicted by the model; and generating the hyperlattice using the model as configured with the selected parameters.

In further, related embodiments, the parameters of the model may be selected to minimize least squared error between the calibration information and results predicted by the model. The reference part calibration information may comprise maximum likelihood information. The reference part calibration information may comprise first uncertainty distributions. Selecting parameters may comprise selecting second uncertainty distributions for the model parameters so that a predicted uncertainty distribution for a future condition matches the first uncertainty distribution. The uncertainty distribution may be selected with constructive and destructive cumulative uncertainty from uncertainty sources. The uncertainty sources may comprise at least one of model input, operating condition, sensor error, ground truth errors in calibration data, ground truth error in recalibration data, and ground truth errors in population data. The model may be a fracture mechanics model.

In another embodiment according to the invention, there is provided a computer-readable storage medium comprising computer-executable instructions that, when executed by at least one processor, perform a method for estimating uncertainty of a predicted condition of a component at a future time, the method comprising: estimating a probability distribution function for a current condition of the component; and estimating uncertainty of a future condition of the component at the future time by performing a plurality of look-up iterations on a hyperlattice to construct a probability distribution function for the future condition of the component.

In further, related embodiments, the method may further comprise: executing a model to produce a result for each of a plurality of input conditions, each input condition specified by a value for each of at least one input variable, wherein the at least one input variables are each varied over a respective range of values to produce the plurality of input conditions; and forming the hyperlattice, the hyperlattice comprising each of the results in association with the respective input condition. The model may be a facture mechanics model for fatigue crack initiation and growth on a metal component, and the inputs that are varied may be initial crack size and material properties, and the database may be configured with two dimensions including remaining fatigue life and a sum of applied and residual stress at a critical location, and the measured quantities may be equivalent cycles and a digital NDT response at two or more times, and the digital NDT data may first be used to estimate the likely crack distribution at a first inspection time during service and then used to predict the a future condition and uncertainty related to crack growth.

The foregoing is a non-limiting summary of the invention, which is defined by the attached claims.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 9A shows a set of plots illustrating probability distributions for inputs into a hyperlattice;

FIG. 9B is a block diagram illustrating operation of a prediction module according to some embodiments;

FIG. 9C is an example cumulative distribution function output from a prediction module;

DETAILED DESCRIPTION OF THE INVENTION

Figure 1:
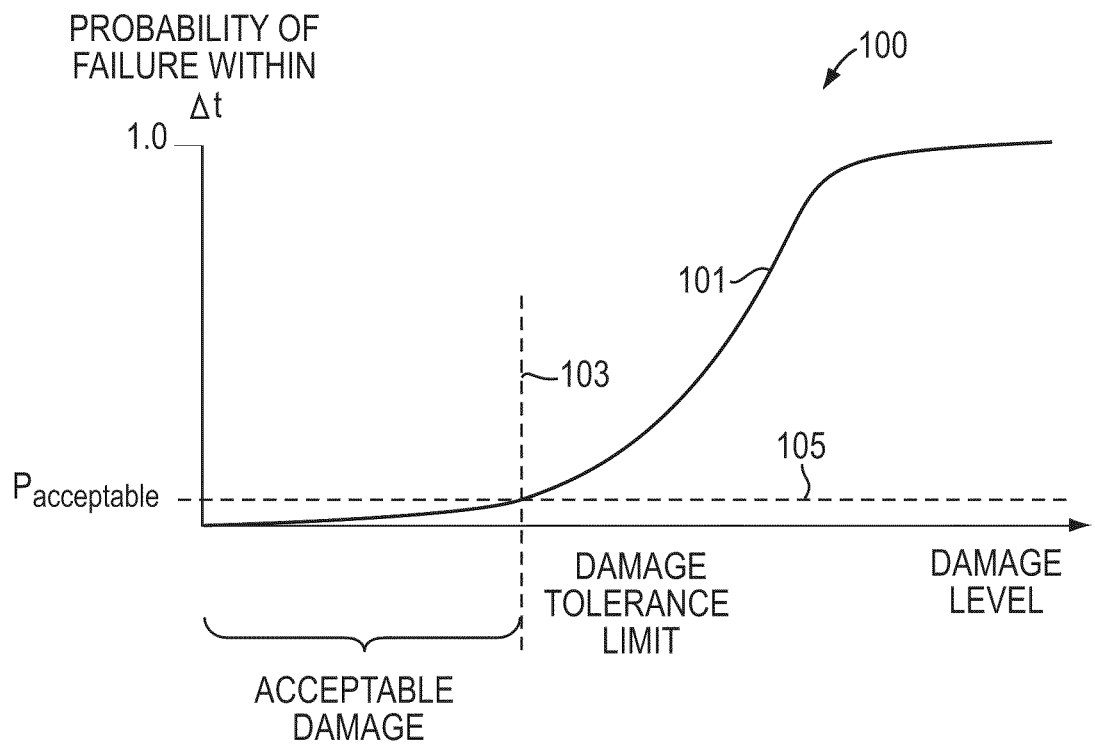
FIG. 1 is a plot sketching the probability of failure within a time $\Delta t$ given a current damage level of a component.

A framework is provided for adaptively managing the life of components. The framework provides a system for accurately predicting component life, scheduling component inspections, and a decision making process for maintaining and replacing components. The inventors have recognized and appreciated that remaining component life is inherently probabilistic and that using information collected in a sequence of inspections may significantly improve estimates of components life, improve scheduling of inspections, and improve the decision making process for performing conditions based maintenance (CBM) actions.

As used herein a "component" is any type of physical part or device. In some embodiments, a component may be a constituent of a device. Though, a device, regardless of its number of constituent parts, may be a component. Examples of types of components include rotorcraft components, fixed wing aircraft components, drill pipe connections, oil pipelines, composite skins, and medical implants. In some embodiments a component is a part of an aircraft, such as an airplane, glider, or helicopter, or UAV. Though, it should be appreciated that the framework may be used with components of any suitable type.

Components may be made out of any suitable material or combination of materials. For example and not limitation, component may be made of materials such as metals, alloys, ceramics, asphalts, transparencies, rubber, glass, cable bundles, composites, and matrix/fiber materials such as carbon fiber reinforced composite. Some components may be made up of a combination of materials. For example, a component may include several material layers. The layers may include different materials and may feature materials of the same type but at different orientations with respect to one another. For example, a component made from a fiber based composite may include a stack up of multiple layers with the same or differing orientations of the fibers. Practitioners may refer to a component as a "critical component" if in-service failure of the component is unacceptable.

Components may be shaped or used in such a way as to have one or more features at which the fatiguing effects of the operating conditions are more significant than other locations on the component. As such, growth of flaws to a critical size at any of these locations may represent the likely failure modes for the component. Practitioners may refer to these features as "hot spots," "control points," or "fatigue critical locations." Some examples of hot spots may include bolt hole locations, connection points, narrow regions, and other features of the component that tend to be subject to increased damage rates, such as from higher stresses under the component's operating conditions.

During operation a component's condition may deteriorate due to the development and growth of flaws in the material of the component, such as the growth of a crack or the development of deleterious condition such as residual stress relaxation. Deterioration of the components condition may result from the material of the component having a lower residual strength. Such damage to the component may develop near the component's hot spots. Though, it should be appreciated that flaws may develop anywhere on a component. For example, some flaws may be generated by impact damage. While the presence of flaws may foreshadow the onset of reduced functionality or failure of the component, actual reduction in functionality of a component is not required for a flaw to be present as many components are "over designed" to accommodate damage without any reduction in performance. What constitutes damage depends on the function and material of the component, more particularly on the function of the component for which in-service component failure is to be avoided. Examples of damage for components providing mechanical strength made of metals and alloys include metal fatigue, cracks, corrosion, thermal, thermomechanical, and mechanical impact damage. As another example, damage of components providing mechanical strength made of matrix/fiber composites include cracks, impact damage to the matrix and fibers, thermal damage, fatigue, machining effects such as cutting and drilling, damage from mechanical and thermal overloads, and environmental damage such as corrosion.

Adaptive life management may be performed for a single component or a group of components. A group of components of the same type that are being monitored are herein referred to as a pool. A component life management system may perform life management for more than one type of component.

Component lifetime may be measured in equivalent fatigue cycles. Cycles may be defined in any suitable way such as to allow a consistent comparison between, for example, different time periods or different components. Examples of definitions for counting cycles include ground-air-ground (GAG) cycles, and total accumulated cycles (TACs). In some embodiments, cycles may be measured as equivalent usage hours under prescribed operating conditions. It should be appreciated that, unless otherwise stated, use of the word time refers to a chronological progression that may be measured in seconds, equivalent cycles, cycles, or any other measure of chronology in a process.

The risk of failure of a component is the probability of having a flaw grow beyond a critical flaw size. The critical flaw size may, for example, be the flaw size at which the flaw growth rate will increase to a point that will cause failure in the next service period (that is before the next inspection opportunity). Note that the critical flaw size may vary for different features of the component. For example, failure for a crack, may be defined as a point at which the crack size reaches a prescribed crack depth within a predefined set of locations at one or more critical features on a critical component. In some embodiments, laboratory tests may be performed to define the critical flaw size. Though, it should be appreciated that the critical flaw size may be defined in any suitable way.

Figure 2:
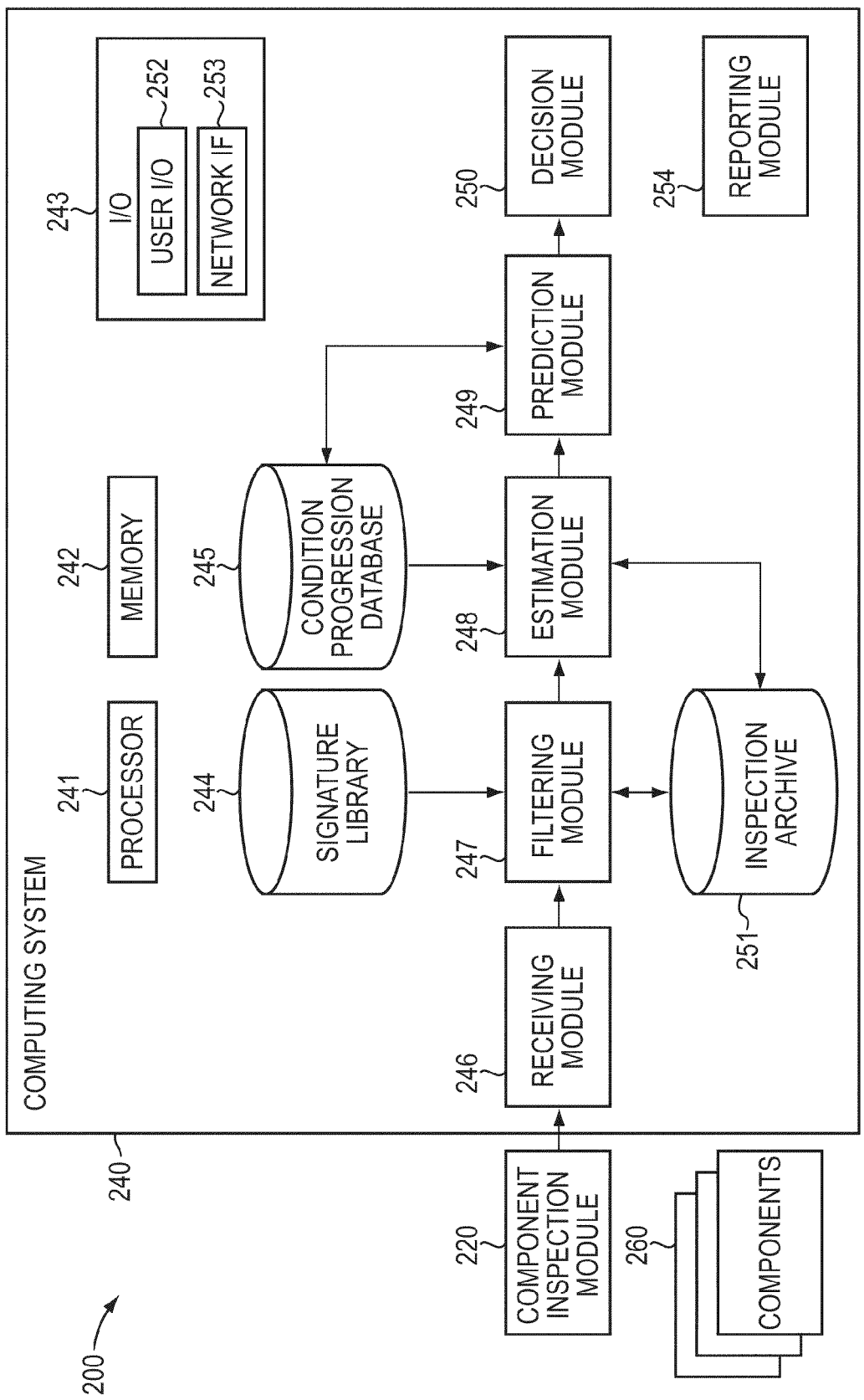
FIG. 2 is a block diagram of an inspection system according to some embodiments.

FIG. 2 is a block diagram of an inspection system 200 according to some embodiments. Inspection system 200 includes a component inspection module 220 and a computing system 240.

Component inspection module 220 obtains inspection data by inspecting a component 260 and provides this inspection data to computing system 240. In some embodiments, component inspection module 220 includes sensors for performing a non-destructive test (NDT) of component 260. The sensors may provide good repeatability from scan to scan such that comparison between inspection data taken at different cycles is practical. In some embodiments, component inspection module 220 may use an electromagnetic based sensing technology, an ultrasonic based sensing technology, or any other suitable sensing technology or combination of technologies. For example an eddy current sensor, such as a meandering winding magnetometer (MWM) sensor, may be used to inspect components. As another example a capacitance sensor, such as a dielectrometry sensor, may be used to inspect the component.

In some embodiments, component inspection module 220 provides a high resolution imaging of a component in, for example, one, two, or three spatial dimensions. NDT inspections may produce a one, two, or higher dimension record/image that relates to the material condition over a surface or volume of a component or other material configuration. The inspection data may be digitized for storage in a computer-readable storage medium. NDT inspection methods that produce digital data may be referred to as "digital NDT". The sensor may image some measure of damage or some property of the material that is related to damage such as the microstructure or micromechanical features of the component's material. In some embodiments one or more electrical properties of the component's material are imaged by the component inspection module 220. The measured electrical properties may be related to damage features.

Components 260 may be one or more components that are being inspected. Components 260 may be any suitable type of component, may be a pool of components of the same type, or multiple pools of components. In some embodiments, components 260 are components of a fleet of aircraft.

Computing system 240 may be any suitable type of computer configured to receive and process sensor data from component measurements. In some embodiments, computing system 240 comprises a plurality of computers. The computers may be operably connected via any suitable networking technology. In some embodiments, inspection module 220 and a computing system 240 are integrated into a single unit, for example, a handheld device. In some embodiments, inspection module 220 and a computing system 240 may be separate units. Though, inspection module 220 and a computing system 240 may be provided in any suitable way.

Computing system 240 has a processor 241 operably connected to a memory 242. Processor 241 may be any suitable processing device such as, for example and not limitation, a central processing unit (CPU), digital signal processor (DSP), controller, addressable controller, general or special purpose microprocessor, microcontroller, addressable microprocessor, programmable processor, programmable controller, dedicated processor, dedicated controller, or any other suitable processing device. In some embodiments processor 241 comprises one or more processors. For example, processor 241 may have multiple cores and/or be comprised of multiple microchips.

Memory 242 may be integrated into processor 241 and/or may include "off-chip" memory that may be accessible to processor 241, for example, via a memory bus (not shown). Memory 242 may store software modules that when executed by processor 241 perform a desired function. Memory 242 may be any suitable type of computer-readable storage medium such as, for example and not limitation, RAM, a nanotechnology-based memory, one or more floppy discs, compact discs, optical discs, volatile and non-volatile memory devices, magnetic tapes, flash memories, hard disk drive, circuit configurations in Field Programmable Gate Arrays, or other semiconductor devices, or other tangible, non-transient computer storage medium.

Computing system 240 also includes suitable input/output (I/O) 243. I/O 243 comprises any suitable hardware and software for interacting with computing system 240. For example, I/O 243 may include a user I/O 252 and a network interface 253.

Network interface 253 may be any suitable combination of hardware and software configured to communicate over a network. For example, network interface 253 may be implemented as a network interface driver and a network interface card (NIC). The network interface driver may be configured to receive instructions from other components of computing system 240 to perform operations with the NIC. The NIC provides a wired and/or wireless connection to the network. The NIC is configured to generate and receive signals for communication over network. In some embodiments, computing system 240 is distributed among a plurality of networked computing devices. Each computer may have a network interface for communicating with other the other computing devices forming computing system 240.

Computing system 240 may include one or more databases such as signature library 244, condition progression database 245, and inspection archive 251. The databases may be stored in memory 242, though this is just an illustrative embodiment and other storage locations are possible.

Signature library 244 is a library of sensor responses for component flaws. Signatures may be generated from experiment, analytical models, computer simulation, any suitable combination thereof, or in any suitable way.

In some embodiments, a study is performed on simple elements and/or representative fatigue test articles to generate crack signatures. Simple elements or simplified elements are elements, coupons or otherwise representative configurations of a material of interest. Simple elements may be processed (e.g. fatigue tested, heat treated, shot peened, machined) in a manner representative of the behavior of interest and NDT data is recorded on the simple elements at different times or stages within the process at prescribed locations within the material volume. A representative fatigue test article may be a simple element or a more complex element that represents a fatigue critical location on a component.

A suitable coupon may be made of the same material as the component to be inspected. Baseline sensor measurements of the coupon may be taken, for example, before a crack develops. The coupon may then be fatigued by an applied cyclic load. The coupon may be scanned periodically using the inspection sensor as a crack develops. A secondary measurement technique may be used to characterize the crack such that the resulting scan may be identified with the "actual" crack characteristics. In some embodiments, acetate replicas or fractography may be used. The inspection sensor data is used to locate cracks in the replicas for larger crack sizes so the earlier replicas can be used to locate the cracks before sufficient sensor signal-to-noise existed for reliable detection.

The secondary measurement technique may provide a direct measurement of the flaw size. Though, any suitable measurement technique may be used. The secondary measurement technique may be another non-destructive testing technique. Though, in some embodiments a destructive measurement technique is used. It should be appreciated that the secondary testing technique may not be suitable for field measurements of the component. This may be due, for example, to the time it takes and/or the cost of performing the secondary measurement.

In some embodiments the flaw signatures are themselves filtered. For example, the flaw signatures may be baseline subtracted. That is, the sensor response to the coupon prior to development of the flaw may be subtracted from the sensor response to the coupon after development of the flaw. The flaw characteristics may be known with high accuracy by using secondary measurement techniques. In another embodiment, a selected signature from the signature library may be used to construct a digital filter to enhance the flaw response and suppress noise.

Computing system 240 may also include inspection archive 251. Inspection archive 251 may store information related to previous component tests, inspection schedules for the components, history of condition based maintenance actions, predicted operating conditions for the component, and any other suitable information related to a component, pool or fleet. In some embodiments, inspection archive 251 maintains information for a number of the same type of component. For example, information may be stored for each component in a pool. Inspection archive 251 may also store statistics generated for a pool and information for different types of components.

Condition progression database 245 stores the execution results for inputs to a condition progression model, which is also referred to as a phenomenological model. The execution results may be tabulated by condition progression database 245 in the form of a hyperlattice. A hyperlattice is an n dimensional nonlinear parameter space generated from a phenomenological model for the growth of component flaws. Here n may be a counting number (1, 2, 3, ...). In the special cases of n=2 and n=3 the hyperlattice is referred to as a grid and a lattice, respectively. The hyperlattice may be used as a look-up table. The phenomenological model and the generation of a hyperlattice is discussed, for example, in connection with FIG. 3, below. In some embodiments, condition progression database 245 may store more than one hyperlattice. Multiple hyperlattices may be stored when different ranges and/or densities of input parameters are used to generate the hyperlattices. Also, hyperlattices may be generated by different models if different types of flaws may be present in a component. For example, different crack morphologies may have different hyperlattices.

In some embodiments, a hyperlattice is a database that is computed using a phenomenological model where one dimension of the hyperlattice is material condition and another dimension of the hyperlattice is a measure of time (e.g., cycles or some chronology). The material condition and measure of time may be measurable, using a sensor or other means, within some finite uncertainty. The hyperlattice may also include at least two additional properties selected for estimation. In one embodiment, the two unknown properties are remaining life and stress. In another embodiment, the properties are crack size and stress where the crack size unknown to be estimated is the same as that measured by the sensor. When the unknown is remaining life, the remaining life may be defined as the time remaining to reach a critical crack size, where the critical crack size may vary with the estimated or predicted applied stress.

A lattice point is a data point in the hyperlattice database. In some embodiments, a lattice point may include at least four values, for example, two measured values and two values of parameters to be estimated. The values of the parameters to be estimated may be generated offline using the phenomenological model for the range of possible values for the two estimated unknowns over the range of the possible values of measured values.

Figure 4A:
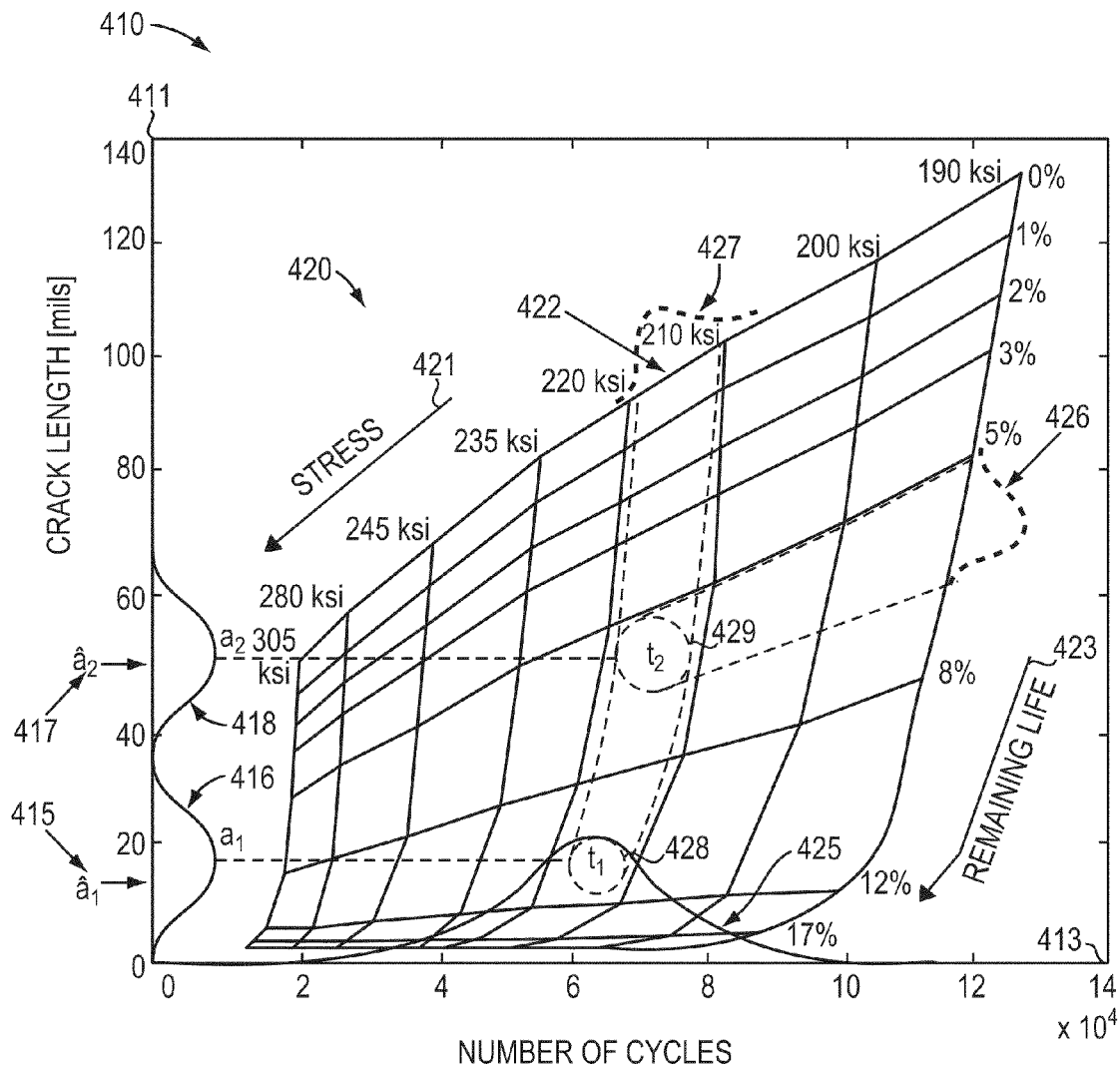
FIG. 4A is a plot illustrating at least a portion of a hyperlattice according to some embodiments.

Plot 410, shown in FIG. 4A, shows an example of at least a portion of a hyperlattice along with some exemplary data to illustrate some aspects of use of the hyperlattice according to some embodiments. In this example, the material condition is crack length which is plotted on axis 411. Time is measured in cycles and is plotted on axis 413. A grid 420 is plotted on plot 410. The parameters estimated by grid 420 are remaining life and stress. Arrow 421 indicates the direction of increasing stress and arrow 423 indicates the direction of increasing remaining life. The crack length may be estimated at inspection time t1 using sensor data. Here the sensor data is characterized by a metric 415, $â_1$. A probability distribution 416 of crack lengths is estimated from $â_1$. A probability distribution 425 estimates the number of cycles the cracked component was in service at inspection time t1. Region 428 in the grid represents regime of likely stresses and remaining life given probability distribution 416 of crack length and probability distribution 425 of number of cycles. A second inspection is also shown at time t2. Metric 417, $â_2$, characterizes the sensor response at time t2. A probability distribution 418 of crack lengths is estimated from $â_2$. A distribution function for the number of cycles may also be estimated for t2 (not shown). From the probability distributions for the crack lengths and the number of cycles at t2 the stress and remaining life of the component may be estimated. The estimated stress and remaining life are represented by probability distribution 427 and 426, respectively. From the lattice it can be seen that the locus of critical crack sizes 422 (remaining life is 0%) predicted from the hyperlattice is at around 100 mils.

Computing system 240 may include computer executable software modules, each containing computer executable instructions. The software modules may be stored in memory 242 and executed by processor 241, though this is just an illustrative embodiment and other storage locations and execution means are possible. In some embodiments, receiving module 246, filtering module 247, estimation module 248, prediction module 249, decision module 250 and reporting module 254 may be implemented as computer executable modules. However, these modules may be implemented using any suitable combination of hardware and/or software.

Receiving module 246 is configured to receive inspection data from component inspection module 220. In some embodiments, receiving module 246 interfaces with component inspection module 220 through a wired or wireless interface. For example, component inspection module 220 may be connected to computing system 240 via a USB, IEEE 1394 connection, through an Ethernet, Bluetooth or IEEE 802.11 network. In some embodiments, a computer-readable storage medium, such as a compact flash disk is used. Though, inspection data may be provided to computer system 240 in any suitable way.

Once the inspection data is received by receiving module 246 the data may be passed to filtering module 247 for filtering. In some embodiments, receiving module 246 stores the inspection data in inspection archive 251.

Filtering module 247 may filter the inspection data to enhance the observability of component conditions of interest and to suppress indications that are not of interest. In some embodiments, filtering module 247 performs baseline subtraction. Baseline subtraction may be performed by spatially registering earlier inspection data with the present inspection data and taking the difference. Earlier inspection data may be obtained, for example, from inspection archive 251. Filtering module 247 may also filter the inspection data using signatures from signature library 244.

Estimation module 248 may estimate the current condition of the component. The current condition may be estimated using previous inspection data, hyperlattice look-ups, or in any suitable way. In some embodiments, the current condition is described probabilistically, for example, by a probability distribution function or a cumulative distribution function. In some embodiments, the distribution function is a Gaussian distribution defined by a mean and standard deviation.

To estimate the current condition estimation module 248 may identify the location of flaws on the component. Flaw sites will promote damage evolution at a faster rate than locations without such damage. The constellation of flaws and their respective types and sizes may be recorded and stored in inspection archive 251. Identifying current flaws may be facilitated in part by flaws that were identified on the component as part of a previous inspection. The location of flaws may be mapped and the evolution of the flaws tracked across inspections. The flaws may be ranked, for example, based on the risk of component failure they present.

Prediction module 249 predicts the future condition of the component at a future time. In some embodiments, prediction module 249 performs a look-up and interpolation in condition progression database 245 to predict the future condition or time. The prediction model may be configured to select an appropriate hyperlattice from condition progression database 245. Selection of the hyperlattice may be based for example, on expert input, the current condition, previous flaw detections, expected flaw growth.

Prediction module 249 may include a rapid, multivariate, nonlinear search tool. The search tool may generate real time estimates of unknown properties of the condition of a component and the uncertainty distribution for those properties.

The flaw sites, types, and sizes may stored by evaluation module 248 in inspection archive 251 may be input to the hyperlattice or the phenomenological models for identifying and bounding the time that new damage sites appear on a component such as a metal dynamic rotorcraft component, or a composite wing skin or propeller blade or on an oil pipeline.

After the future condition and/or future time have been predicted, decision module 250 may determine what action, if any, should be scheduled or made for the component. In one such embodiment, if the mechanical/impact damage level is below a threshold that enables it to remain in service (even though it was detected and documented by the sensing method) then it is valuable to map and track these sites, and to record the time at which they appeared. Then the damage evolution can be monitored for each site to assess risk, and the possible interaction of sites that are close enough to increase risk of failure, can be incorporated into models. Decision module 250 may schedule a next inspection of component, determine that the component should be replaced, and/or determine that the component should be repaired. Inspections may be scheduled at equal intervals or spaced in sequences that improve flaw growth rate (derivative) estimation or in any other pattern that improves estimation or prediction of component conditions.

Figure 3:
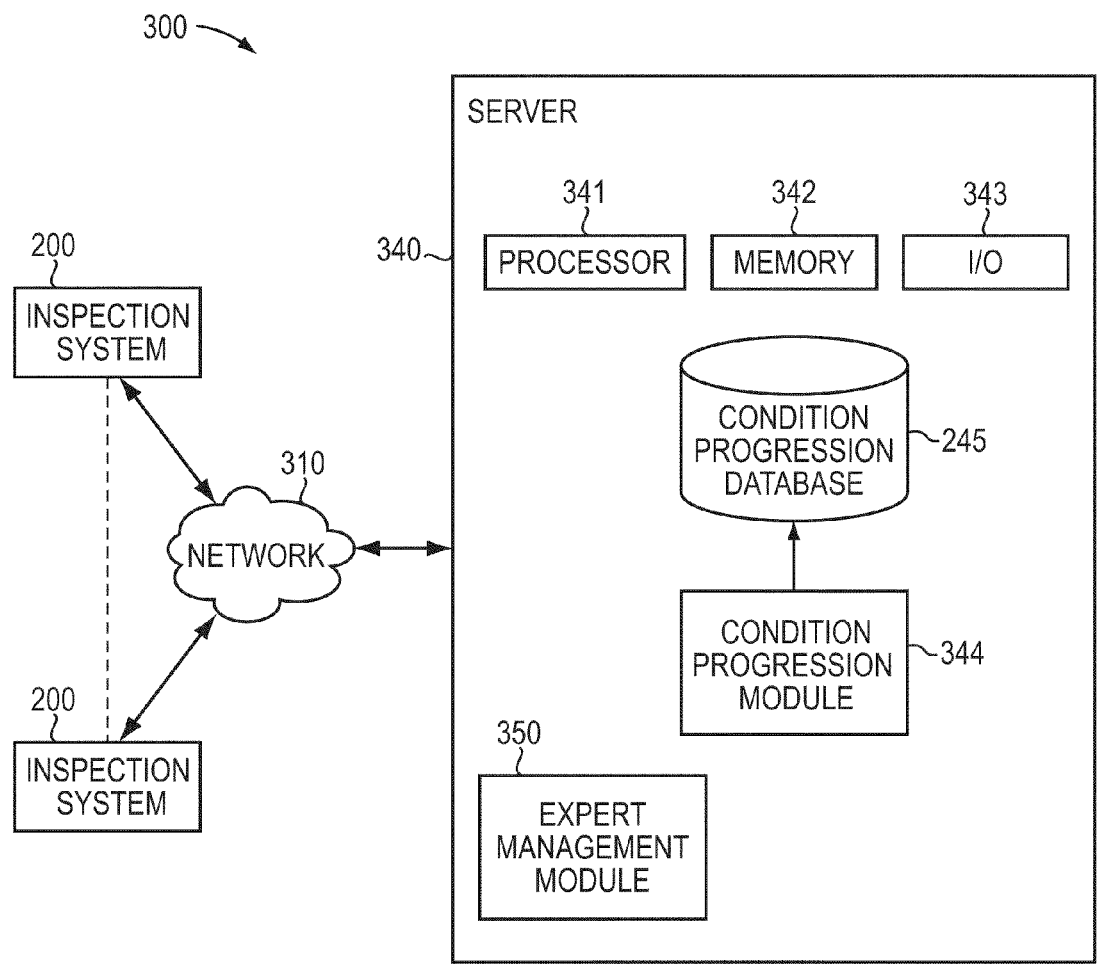
FIG. 3 is a block diagram of a system for distributing hyperlattices to inspection systems according to some embodiments.

Condition progression database 245 may be periodically updated to reflect additional knowledge obtained through the course of managing a pool of components. The underlying models on which the hyperlattices are generated may be adjusted, for example, to correct estimated parameters and assumptions that are better understood. In some embodiments, a system 300, shown in FIG. 3, is used to distribute condition progression database 245. In some other embodiments, computer system 240 may include models for generating the hyperlattices for condition progression database 245 (FIG. 2).

A reporting module 254 may be configured to generate reports documenting the inspection, detection of flaws, estimated conditions and predicted conditions, the action to be taken for the component, and the like. Reporting module 254 may populate a database that may be accessed by administrators and experts. In some embodiments, the database may be accessed over a network. In some embodiments, reporting module 254 generates a word processor document report. The report may be printed out or stored on a computer, for example, in association with the component.

As shown in FIG. 3, server 300 may be connected to one or more inspection systems 200 (see also FIG. 2) via a network 310. An updated version of condition progression database 245 may be downloaded from server 340 to the respective inspection systems 200. In some embodiments, only some hyperlattices stored in condition progression database 245 of server 300 may be downloaded to particular inspection systems. The availability of hyperlattices may be determined, for example, based on licensing arrangements.

In some embodiments, inspection systems 200 may also upload inspection data, statistics, component conditions, and the like to server 340. Server 340 may have a processor 341, memory 342 and I/O 343 similar to those described for processor 241, memory 242, and I/O 243 above (see FIG. 2).

Figure 4B:
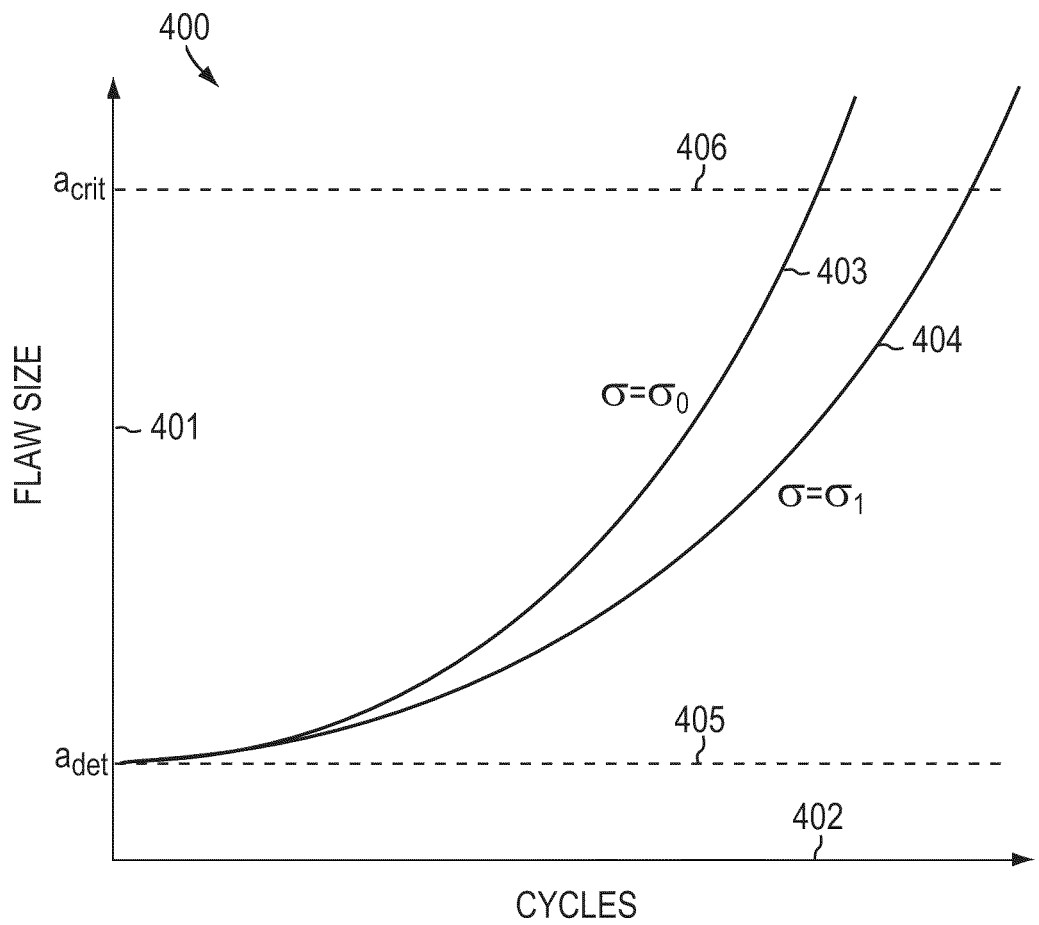
FIG. 4B is a plot showing predicting flaw growth in a component under different operating conditions.

Hyperlattices stored in condition progression database 245 may be generated by a condition progression module 344 which provides a phenomenological model for predicting the evolution of component damage or anticipating kinematic, static, dynamic environmental or material changes in the component. The flaw growth rate predicted by the model may depend on the operating conditions incurred during each cycle by the component. Different operating conditions may result in different time period for growing a flaw to its critical size. Plot 400, shown in FIG. 4B, is a sketch of two different flaw growth curves for two different operating conditions. Specifically, plot 400 illustrates the growth in flaw size (axis 401) as a function of the number of operating cycles (axis 402). Curve 403 is a flaw growth curve for stress $\sigma_0$ and curve 404 is a flaw growth curve for stress $\sigma_1$. Both curves assume the same initial condition for the component. As sketched, $\sigma_0 > \sigma_1$. Also marked in plot 400 are the detectable flaw size 405 and the critical flaw size 406. The detectable flaw size is a flaw that can be detected with a defined probability of detection (POD) with a defined probability of false alarm (PFA). The POD and PFA of the detectable flaw size may, for example, be specified to suitable levels for a specific application.

The phenomenological model may predict component conditions such as how flaw size affects the sensor response, property (such as effective electrical conductivity or magnetic permeability) variations with impact damage, thermal changes in electrical properties, dielectric constant changes with thermal exposure, and any other suitable property of the component and how the property affects sensor response. The model may be component specific, and may be tailored for the materials used to construct the component.

The phenomenological model may be physics based (e.g., fracture mechanics model, fatigue model), system dynamics based, parametric, logic based, empirical study based, or based on field and production experience, or any suitable combination thereof. Though, any suitable type of phenomenological model may be used. In some embodiments, different phenomenological models are used to model the evolution of different types of flaws. A crack, for example, may have several different morphologies. A cracks may develop as long and shallow discrete crack, a cluster of similarly sized microcracks, or a cluster of variable sized small cracks with one larger crack. The evolution of these crack morphologies may be modeled using different phenomenological models and accordingly, different hyperlattices may be produced. The models may also account for the proximity of damage sites on a component as flaws located sufficiently near one another may have a different damage progression path than in isolation. In some embodiments, the phenomenological models may be provided and modified by one or more experts in the relevant technical arts.

The phenomenological model may be used to generate a hyperlattice of conditions of the component. The input conditions used to generate the hyperlattice from the model may be derived from laboratory studies of the component's material, knowledge from experts such as original equipment manufacturers (OEMs). For example, input conditions may be determined from coupon studies of crack initiation and growth in a representative environment. Though, any suitable source may be used to determine the inputs for the phenomenological model.

The phenomenological model and resulting hyperlattices may be calibrated to improve their predictive power by using reference part calibration or standardization techniques. In some embodiments, server 300 may provide the uploaded information collected from inspection systems 200 to the experts as feedback for actual component damage evolution. Also, retired component may fatigued to actual failure while collecting fatigue related data. Such a test may be used to determine the actual remaining life of a component. In some embodiments, a retired component may undergo secondary testing (destructive or non-destructive) to determine the actual condition of the component at retirement. This information may be used to reconfigure the phenomenological models to better agree with historical data, generate improved hyperlattices, provide improved uncertainty estimates, usage estimates, initial flaw size estimates, inclusion density, grain decohesion propensity, surface roughness, residual stress, mechanical damage conditions, and the like.

In some embodiments certain model parameters may be modified to produce model outputs that agree with reference part calibration data, fleet sensor measurements, values based on expert knowledge, or the probability distribution of sensor measurements for a similar component. The parameters may represent, for example, the material condition such as residual stress distribution, assumed inclusion density and assumed initial crack size distribution. Though, the parameters may represent any suitable variable. In some embodiments, the reference part calibration data represents the condition of a component after a known number of cycles and given stress level. Accordingly, the initial assumptions about the material at completion of manufacturing (i.e., at 0 cycles) may be adjusted such that the phenomenological model predicts the condition of the reference part at the known number of cycles for the given stress level. As a specific example, the assumed distribution function (e.g., maximum likelihood value and uncertainty) of the initial inclusion size may be adjusted to match the distribution function of the condition of a pool of coupons or components at the given time in the future and for a given stress level. Though, other sources of the distribution function may be used as well. For example, expert knowledge may be used to estimate distribution functions for a defined number of cycles and given stress level. Uncertainty may be selected with constructive and destructive cumulative uncertainty from multiple sources such as model input, operation conditions, sensor error, ground truth errors in calibration data, recalibration data, and population data.

In some embodiments, the hyperlattice is assumed fixed and the inspection sensor responses, usage and other measured data are calibrated to match the hyperlattice. In the case where the hyperlattice is assumed fixed, inspection data may be taken using the component inspection module on components or samples with known properties. A transformation is applied to the inspection data such that the transformed inspection data is in agreement with the hyperlattice. In some embodiments, a transformation may include an adjustment to the effective cycles to match the reference calibration data to the hyperlattice. In some embodiments, flaw size estimation filters are adjusted as part of the transformation to match hyperlattice predictions and other ground truth data. The determined transformation may then be applied to inspection data that is taken on samples with unknown properties for other estimation and prediction computations. Further aspects of this calibration technique may be found in ASTM-E2338.

Server 300 may also include an expert management module 350 for managing the experts that define the phenomenological models of condition progression module 344. For example, module 350 may provide a tool for enabling a team of experts to work together to refine the phenomenological models. In some embodiments, expert management module 350 provides a web based interface and/or portable device for experts to access inspection data, coupon data, the current phenomenological models, hyperlattices, and any other information relevant to defining the phenomenological models or assessing its performance. Expert management module 350 may limit information access to individual experts according to their respective access rights. Some experts may be given a supervisory role to control versions of the phenomenological models and scrutinize the work of other experts to ensure the reliability of the phenomenological models and the hyperlattices generated therefrom.

Figure 5A:
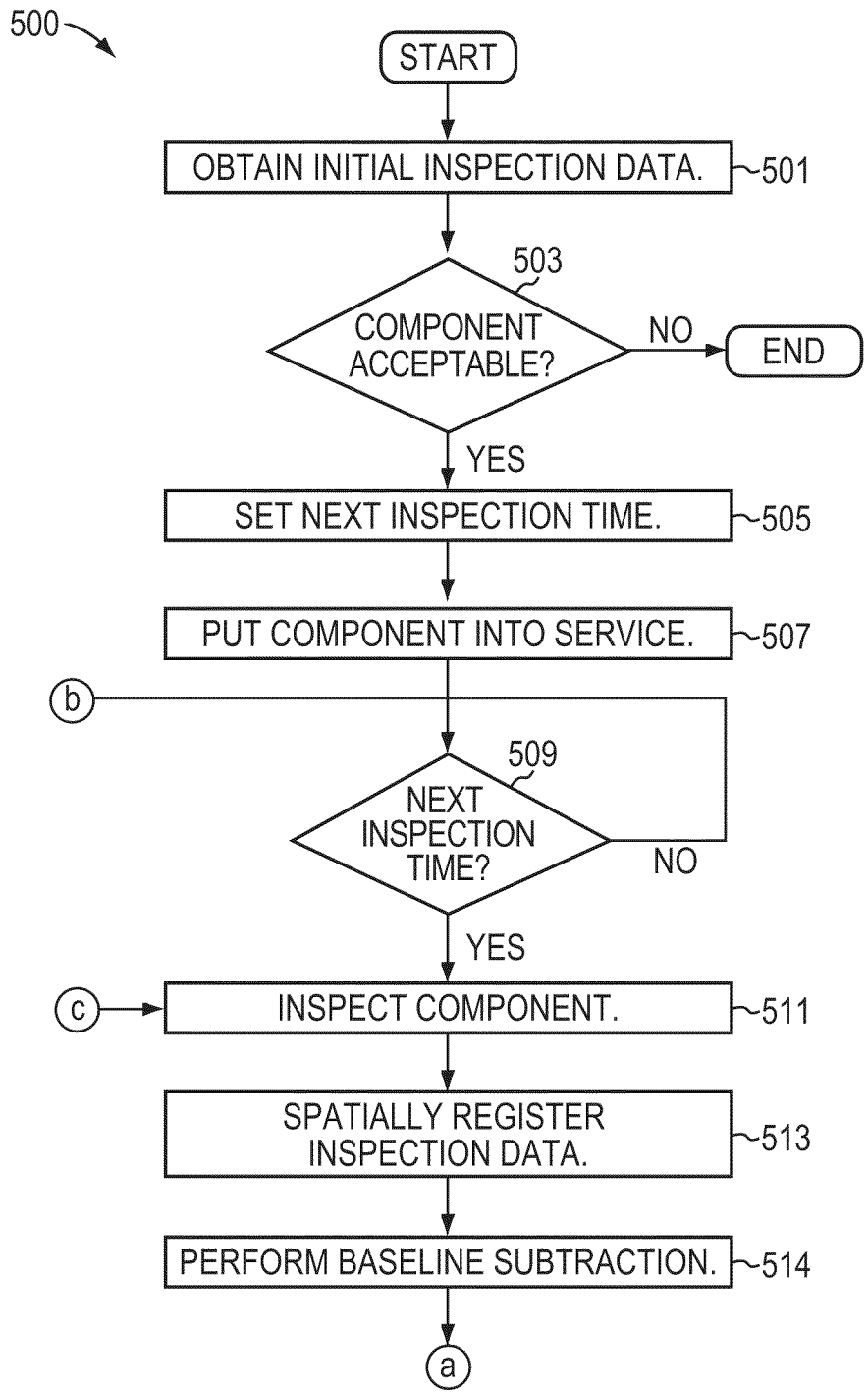
FIGS. 5A-5B is a flow diagram of a method for adaptively managing the life of a component according to some embodiments.
Figure 5B:
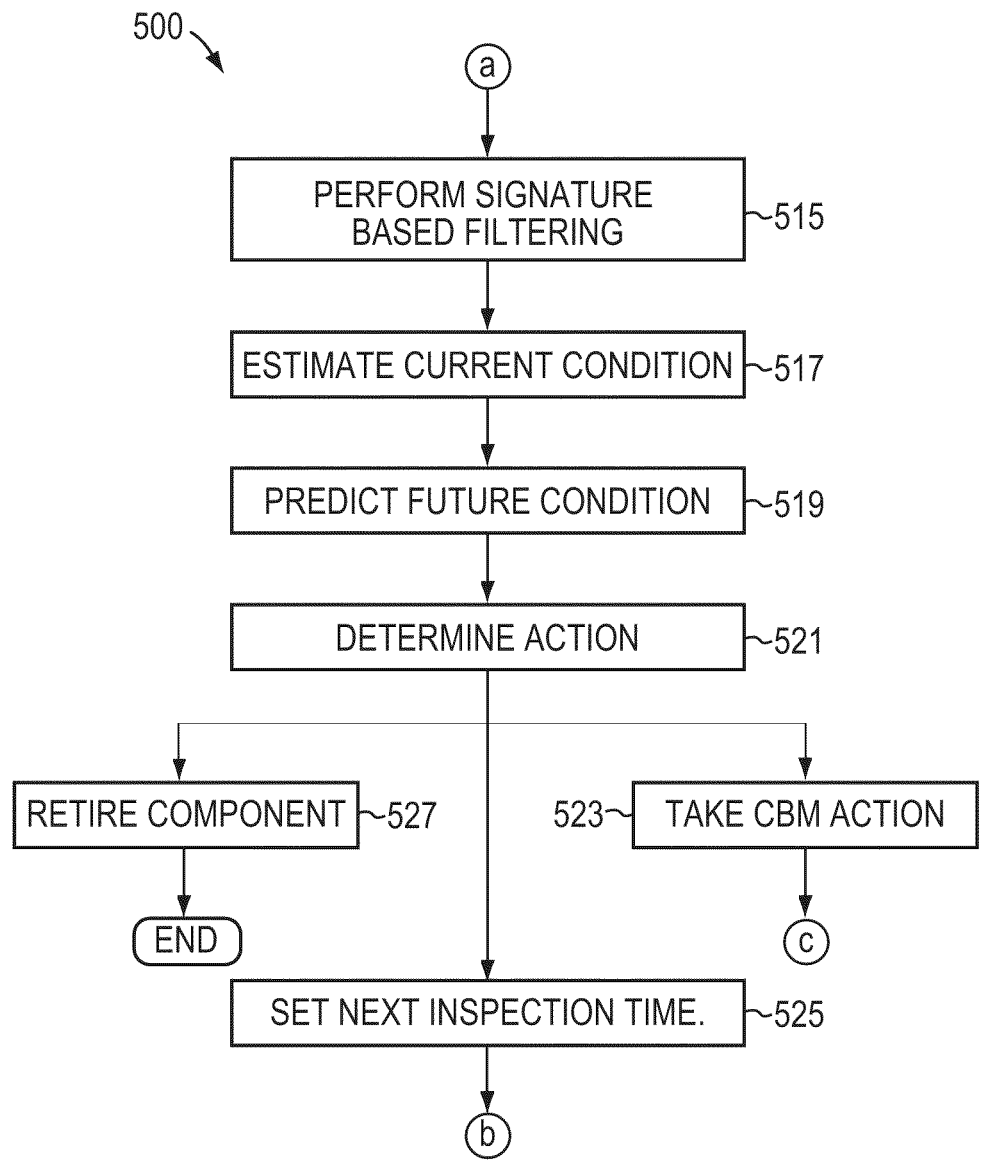

Method 500, shown in FIGS. 5A-5B, is a method of adaptively managing the life of a component. Method 500 may be implemented in any suitable combination of hardware and software. For example, method 500 may be implemented in inspection system 200. In some embodiments, steps of method 500 are stored as instructions on a computer-readable storage medium. When the instructions are executed, the corresponding method step maybe performed. In some embodiments, a graphical user interface may guide an operator through performance of various steps in the method.

It should be appreciated that the steps of method 500 may be performed in any suitable order and FIGS. 5A-5B merely illustrate method 500 according to some embodiments. It should also be appreciated that in some embodiments some steps of method 500 may be optional.

At step 501, initial inspection data is taken for a component. This initial data may be taken prior to putting the component into service. For example, the initial inspection may be done at the end of the manufacturing process. Inspection may be performed for the entire part or may be limited to a set of locations such as hot spots representative of the most probable failure modes for the component.

In some embodiments, inspection data is collected during manufacturing as well. For example, the component may be inspected before and after certain manufacturing steps. A component may be scanned before and after, heat treating, surface treatments (e.g., shot peening) and the like. In some embodiments, the same inspection technique is performed multiple times. By taking multiple measurements at each point, instrument and setup noise may be suppressed by averaging. In some embodiments, inspection data may be taken in multiple orientations. For example, a component made of a material with anisotropic conductivity may be scanned in multiple directions with a MWM-Array sensor to determine the conductivity in different directions.

Figure 6A:
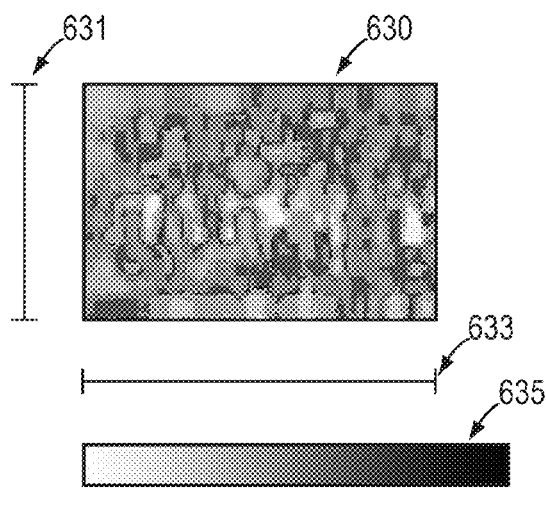
FIG. 6A is an example presentation of inspection data according to some embodiments.

Plot 630, shown in FIG. 6A, illustrates an example of inspection data on a component. In this example, the inspection sensor is an MWM-Array sensor, and the surface conductivity is the material property being plotted in grayscale. Axis 631 and 633 may give the physical dimensions in the respective directions such that the conductivity data may be associated with a particular point on the component. Scale 635 shows the conductivity scale. In some embodiments, the scan results are presented to the operator and the operator may confirm the inspection.

In some embodiments, metadata is provided for the component being inspected at step 501. The metadata may contain information such as the type of component, a serial number for the component, identification of a device the component is part of (if any), the type of material the component is made of, the sensor being used to obtain inspection data, the material of the component, any special treatments performed to the component such as surface treatments, any previous condition based maintenance actions performed on the component, information about the operator, information about the conditions of the measurement such as date, time, temperature and humidity, risk tolerance levels, and any other suitable information. The metadata may be used in the performance of method 500.

Figure 6B:
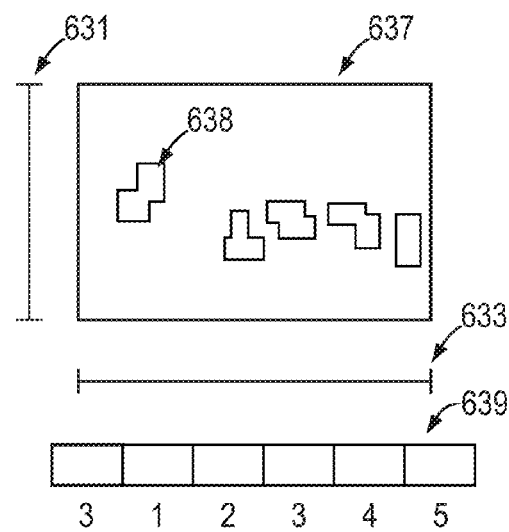
FIG. 6B is a example presentation of indications identified from inspection data according to some embodiments.

At step 503, it is determined whether the component is acceptable to be put into service. The determination may be based, for example, on the initial inspection data collected at step 501. In some embodiments, the initial inspection data is processed to identify areas of possible concern. For example, if the inspection data indicates surface conductivity, a local drop in conductivity may be indicative of a potential crack in the material at that location. Indications may be ranked based on the likelihood that they represent a flaw in the component. The indications may be presented to an operator for review. Plot 637, shown in FIG. 6B, shows an example of how indications may be represented for a component. In this example the top five ranked indications 638 are shown. However, any suitable number of indications may be ranked and presented. Legend 639 presents the ranking. Here, zero represents the unranked space of the component. Axis 631 and 633 provide reference to position on the component for plot 637.

Figures 6C, 6D, 6E:
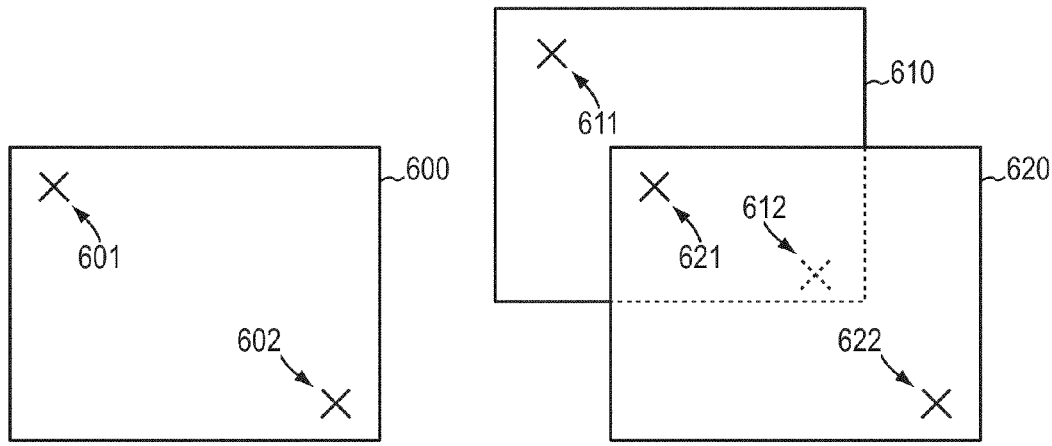
FIG. 6C is an example user interface for receiving input from an operator that indicates further actions to be performed for a set of indications.
FIG. 6D is a sketch of a component with markers for facilitating spatial registration of multiple sets of inspection data imaged from the component.
FIG. 6E is an illustration of an alignment process for two sets of inspection data that utilizes the images of markers on the inspected component.

In some embodiments, the operator is given the option to determine how the indication should be treated. For example, the operator may reject the component based on the indication, may indicate that the indication is not actually a flaw, or may indicate that the indication should be tracked in future inspections. In some embodiments, the operator may provide a comment regarding the decision. The comment may be stored, for example, in metadata along with the inspection data. Window 640, shown in FIG. 6C, illustrates an example user interface for the operator. Window 640 shows the top indications 641, their position 642, and their sensor response 643, â ("a hat"). (Determining the sensor response is discussed, for example, in connection with step 517, below.) A status field 644 allows the operator to select a status for the indication (e.g., reject component, track indication, ignore indication). Additionally a comment field 645 may be used by the operator to input information about the selection. Once the operator is satisfied, "Validate" button 646 may be selected.

If the component is rejected at step 503, method 500 ends. If the component is accepted at step 503, method 500 continues to step 505.

At step 505, the next inspection time is set. The inspection time may be an actual time or may be a number of cycles. The next inspection time may be determined based on the initial inspection data, fatigue tests performed on coupons and representative components, expected operating conditions for the component once it enters service, damage evolution models for the component. In some embodiments, the next inspection time is set by assuming the largest undetectable flaw and using the damage evolution model to predict a time when the flaw has progressed to a certain level (e.g., 20% of critical flaw size). The next inspection time may be set as the predicted time. Confidence in the initial condition may also affect selection of the next inspection time. In some embodiments the next inspection time is chosen as a range. This provides some flexibility as to when the inspection may take place. This may be useful, for example, when the component and component inspection module are only periodically collocated. For example, a component inspection module may be located at an airbase where an aircraft lands. In another embodiment, a pair of future inspection times (or cycles) are selected to improve observability of flaw growth rates.

In some embodiments, inspection after a certain number of cycles may be desired, however, it may not be practical, or possible measure cycles directly. Accordingly, an actual time may be chosen for inspection based on a prediction of when the desired number of cycles will be reached.

In one embodiment, at step 507, the component is put into service. Once the component is in service it is periodically inspected in accordance with steps 509-525. As shown in the flow diagram of method 500, these steps form a loop that are repeated until it is determined to retire the component.

At step 509, it is determined whether it is time for the next inspection. When the next inspection time is easily countable such as for an actual time or a number of GAG cycles step 509 may be determined directly. In some embodiments, it is determined that it is time for the next inspection only if the actual number of cycles is within an inspection range and the component and component inspection module are collocated. Of course, if inspection is an actual time (e.g., Jun. 5, 2009) it may be determined that the time for inspection is at that date. Step 509 loops until it is determined that it is time to inspect the component. The time between inspections is not necessarily equal. It may be set, for example, based on risk of failure before the next inspection.

At step 511, the component is again inspected. Inspection may be performed in ways similar to those described in connection with step 501. The inspection may be performed using a component inspection module such as component inspection module 220 (FIG. 2). As before multiple measurements at each location on the component may be taken to average out noise. Inspection data may be presented, for example, in ways similar to plot 630 (FIG. 6A). Though, it should be appreciated that inspection data may be presented in any suitable way.

At step 513, the inspection data obtained at step 511 is spatially registered with inspection data obtained during a previous inspection. Spatially registering the inspection data aligns the inspection data spatially so that the inspection data at the same location on the component an be compared to one another between the two or more different inspections. Spatial registration may also be made with reference to positions on the actual component so that the inspections data can be understood with reference to the physical component.

In some embodiments, the component may have markers that have a unique signature when scanned by the component inspection module. FIG. 6D shows a component 600 with markers 610 and 620. The type of marker being used may depend on the inspection technology. For example, for a conducting part on which inspection data is collected using an MWM array, markers 610 and 620 may be marked using an insulating tape. The presence of the insulating tape may produce a predictable response that will be present in each measurement of the component. FIG. 6E shows inspection data 610 and inspection data 620. Both sets of inspection data clearly image markers 610 and 620. In inspection data 610, markers 601 and 602 appear as marks 611 and 612, respectively. In inspection data 620, markers 601 and 602 appear as marks 621 and 622, respectively. The images are spatially registered by manipulating inspection data 620 such that marks 621 and 622 are aligned with marks 611 and 612, respectively, of inspection data 610. In another embodiment, markers may be existing patterns in the sensor data or the edge of a part or another such geometric feature.

It is noted that the imaging of markers 610 and 620 may also be used to correct for lost position data. For example, in some embodiments a sensor is scanned over the surface of a component. To correlate the sensor data with the physical location of the sensor a position encoder may be used. The position encoder may be, for example, an encoder wheel or an optical tracker (e.g., light emitting diode and photodiode). If the position encoder seems inconsistent with the scan data such as when the encoder wheel jams or loses contact, the detected markers may be used to estimate the location of the sensor.

In some embodiments the markers have a shape that enables alignment in multiple directions. Though, in some embodiments, alignment may be achieved by resolving the location of multiple markers.

At step 514, baseline subtraction is performed between spatially registered images. In some embodiments, other forms of baselining are performed and, generally, baselining may involve any suitable mathematical function and is not limited to subtraction.

Baselining may suppress manufacturing variations while enhancing the observability of flaws in the component. For example, manufacturing variations may produce changes in an observable material property (e.g., conductivity) that are on the same order as changes produced from, say, impact damage. Baseline subtraction will enable the impact damage to be observed, because of the change in properties between the initial inspection data and the later inspection data. The manufacturing variations in a component will not have changed, however, and thus will be suppressed by baseline subtraction. In one such embodiment, subtraction of a previous image (spatially registered to the first image from the same digital NDT method) other than the baseline is performed to enhance noise suppression or improve crack detection and crack growth rate estimation. In one such embodiment, combinations of two or more images are used to create a functional value of each image location that is then used for estimation and prediction. Where the functional value derived from the data at the same location in two or more images. The functional value is also derived at additional locations within at least two images.

To perform the baseline subtraction the earlier inspection data may be subtracted from later inspection data on a point-by-point basis. In some embodiments the resolution and/or spatial position of the samples may be different between the sets of inspection data. Any suitable interpolation method may be used to produce the difference. In some embodiments, the initial inspection data captured at step 501 is used as the baseline to which all future inspection data is compared. In some embodiments, the inspection immediately preceding the current inspection is used as the baseline. Though, any suitable inspection data may be used as a baseline.

Figure 7A:
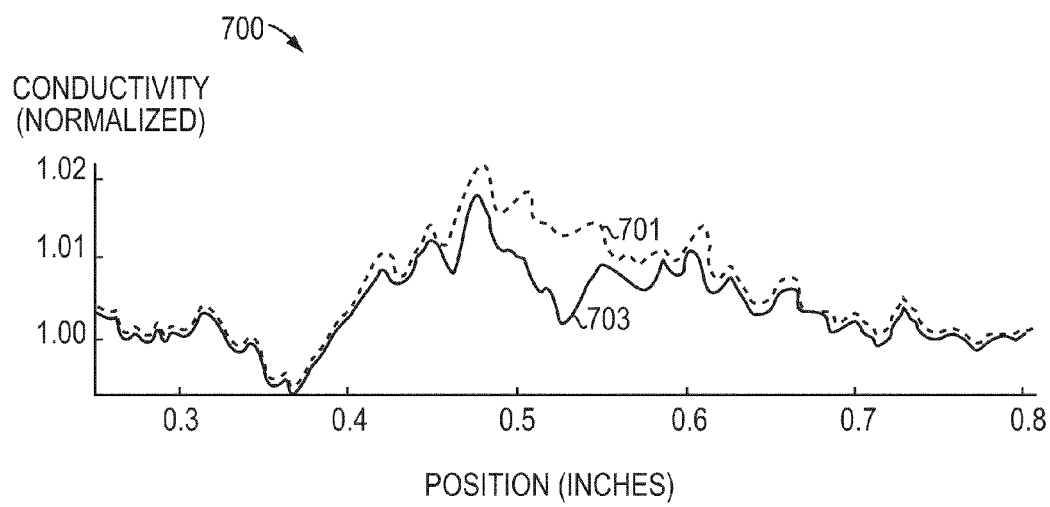
FIG. 7A is a data plot of conductivity data obtained from a titanium alloy sample after 15,000 and 21,000 stress cycles.
Figure 7B:
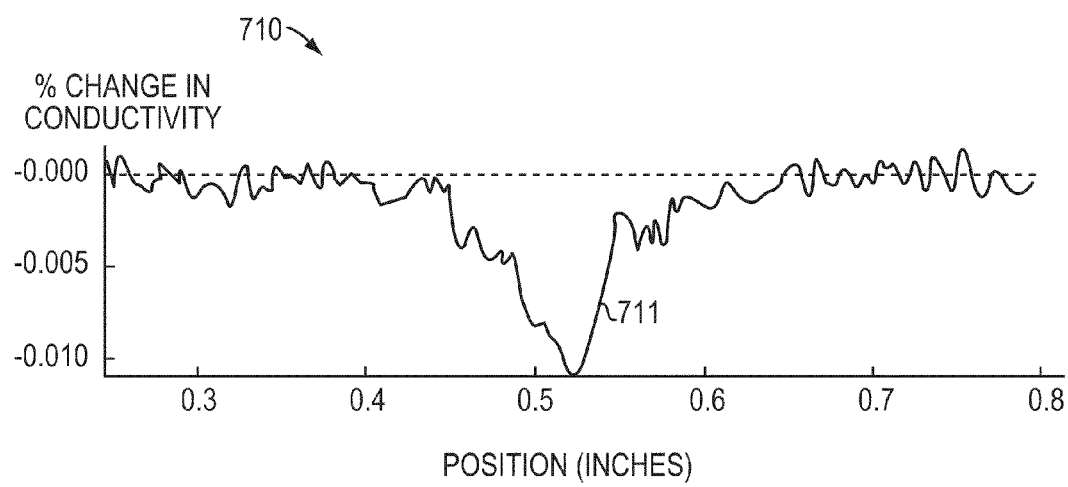
FIG. 7B is a data plot of change in conductivity after baselining the 21,000 stress cycle data with the 15,000 stress cycle data.

Plot 700, shown in FIG. 7A, illustrates the use of baseline subtraction to enhance the visibility of a crack in a titanium alloy (Ti-6Al-4V). Curve 701 shows the normalized conductivity after 15,000 stress cycles. Curve 703 shows the normalized conductivity after 21,000 stress cycles. Both curves 701 and 703 are obtained by averaging 5 repeat scans using a MWM sensor at the respective time. Plot 710, shown in FIG. 7B, shows the change in conductivity curve 711 between 15,000 and 21,000 cycles. The drop in conductivity from the baseline level at around 0.52 inches creates a indicator for a crack that would not be directly identified from curve 703 alone.

It should be appreciated that the operation of baseline subtraction computes the change of the material properties. Knowledge of the time difference between the current inspection and the inspection data used as the baseline (where the baseline is taken from either from digital NDT data at t0 or some other earlier time) may be used to estimate the rate of change in material properties; that is the first derivative. It should also be appreciated that as more inspection data becomes available, for example after each inspection time, higher order derivatives may be estimated. For example, after data from a third inspection becomes available, the rate of change (first derivative) may be estimated using the first in-service inspection and the initial inspection and may again be estimated using the first and second in-service inspection. Accordingly, the second derivate, that is the rate of change in the rate of change, may be estimated. Further, as more inspection data becomes available, the estimates may be refined.

At step 515, the inspection data is filtered using a signature from a signature library. As discussed above, the signature may be obtained from coupon tests of known flaws. In some embodiments, the inspection data is searched for a match to each signature. A match may have the same shape as the signature. A threshold may be set to determine whether a match has been found. If the same location on a component matches multiple signatures, the best match may be chosen for that location. Signatures may be matched at multiple locations on a component. Applying signatures to inspection data results in a POD curve that is steeper than for typical testing methodologies. In other words, flaw sizes below the desired detection threshold are suppressed, while flaw sizes above a desired threshold are detected more readily. In one such embodiment, a function of multiple signatures, perhaps at different frequencies or for different crack sizes, is used to filter the inspection data.

Figure 8A:
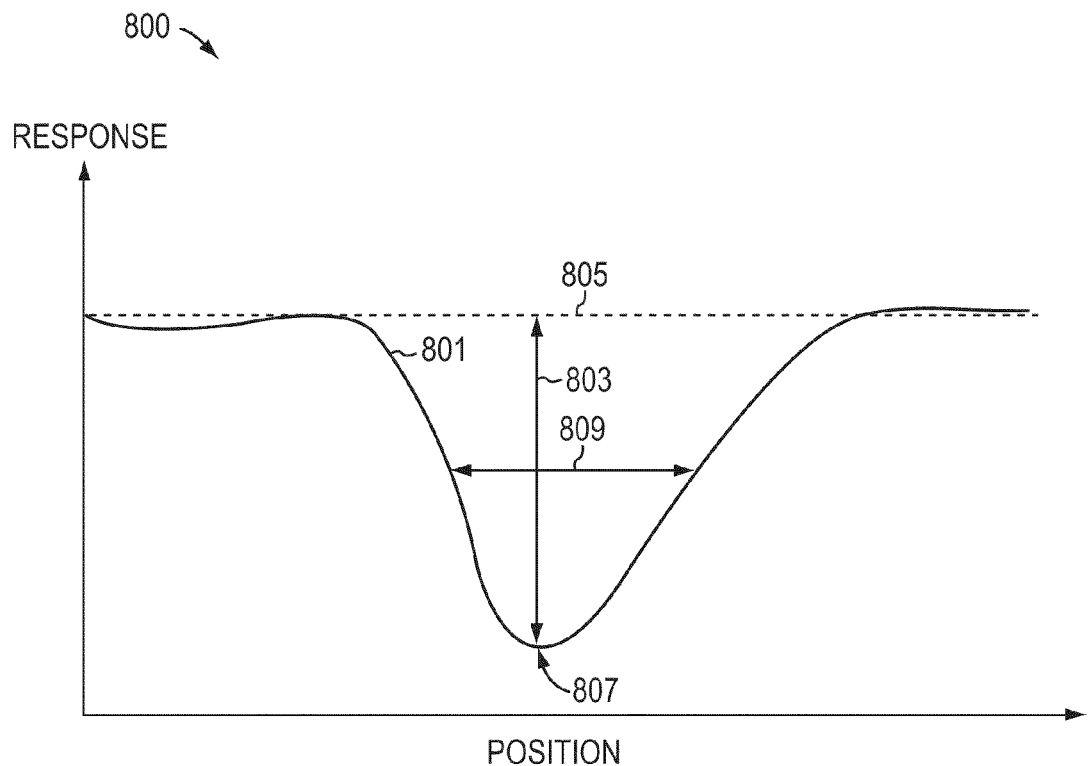
FIG. 8A is a sketch illustrating metrics for characterizing a flaw detection.

At step 517, the current condition of the component is estimated. The current condition may be estimated by characterizing the (filtered) sensor response and using the characterization to look-up the component condition. In some embodiments the sensor response is characterized by a feature height, a feature area, a half-height width, a crack correlation, or in any other suitable way. The feature height may be defined as the peak change in response at a feature relative to the surrounding response. The half-height width may be defined as the width of the feature at half the height. To illustrate, plot 800, shown in FIG. 8A, sketches a sensor response 801 near a feature. Height 803 is the change in sensor response from line 805 to point 807. The half-height width 809 is the distance across the feature at half way up the height 803. These metrics for characterizing a feature observed in inspection data are illustrative. It should be appreciated that any suitable metric may be used to characterize inspection data.

Once the inspection data is characterized, a mapping may be used to determine the component condition. In some embodiments, the mapping is determined experimentally. For example, the sensor response may be measured and characterized for various damage feature sizes in a coupon test. This data may be used to determine the condition of a component by using the sensor response on the component to compute the distribution of crack sizes that is most likely to have produced the sensor response.

Figure 8B:
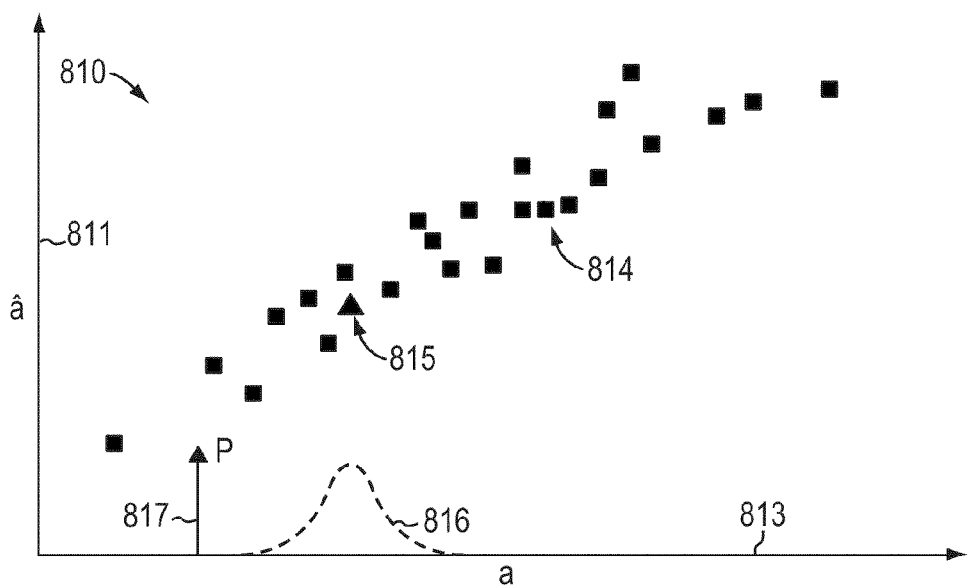
FIG. 8B is an example plot of the measured response to a flaw (â) versus the actual size of the flaw (a)

FIG. 8B shows a plot 810 of example data for a coupon test. Axis 811 represents the characterized sensor response, â ("a hat"). Axis 813 represents a characteristic of the flaw. For example, the characteristic of a crack may be the crack width, crack depth, crack length, crack volume, or any other suitable characteristic or combination of characteristics. In some embodiments, "a" represents the density of cracks. Coupon data 814, represented by the square blocks, may be obtained by performing sensor measurements on flaws that have been characterized using a secondary measurement technique. From the coupon data the correlation between the sensor characteristic response and the characteristic of the flaw may be determined. From the sample data, probability distribution functions may be estimated both for "a" and â.

Also shown on plot 810 is a sensor response 815 for a flaw with an unknown characteristic size, "a". Using the sample data the expected value of the flaw size, "a" may be determined for the sensor response 815. Superimposed on plot 810 is a probability density function 816 representing the probability density 817 of the different flaw size characteristics. For illustrative purposes, sensor response 815 is plotted along axis 813 at the expected value for "a".

In some embodiments, the flaw may be too small to reliably detect using only the inspection data from the current inspection. To determine whether the flaw detected is reliable a threshold may be set for the likelihood that the flaw is smaller than a certain size. For example, it is determined that insufficient information exists to reliably detect a flaw using the current inspection data if the probability of detecting the flaw is below 90%. When insufficient information exists to reliably detect the flaw using the inspection data from the current time, an enhanced response from the inspection may be generated by using inspection data from the current inspection and one or more previous inspection times.

Returning to method 500, at step 519 the future condition of the component is predicted. In some embodiments, the future condition is predicted at a proposed next inspection time. In some embodiments, the future time at which the component condition will have deteriorated to a certain point is predicted. In some embodiments, the method produces a risk of failure as a function of subsequent usage cycles. The prediction made at step 519 may produce a maximum likelihood value and an uncertainty value. In some embodiments, the prediction is simply described by a probability distribution function for the future condition or future time.

Prediction of the future condition may be facilitated by using a mechanism other than direct execution of the phenomenological model. For example, a precomputed database such as the condition progression database 245 (FIG. 2) may be used. In some embodiments, use of a precomputed database allows for real time determination of the future condition, while use of the phenomenological model to predict the future condition may take a considerably longer time. Here, real time is understood to be a time period of a few minutes. For example, two minutes or less. Though, in some embodiments, a real time prediction of the future condition may be a table look-up from the precomputed database in a few to several seconds.

In some embodiments, the estimated current condition and estimated operating condition of the component are described probabilistically. That is, an uncertainty may be associated with the values. If inspection data from multiple inspection data is available, the condition at the respective inspection times may be described probabilistically. Accordingly, the output future condition of the component may also be described probabilistically. A hyperlattice that may be used to account for uncertainty may also be referred to as a fuzzy hyperlattice.

In some embodiments, the estimated current condition, one or more estimated and then predicted operating conditions, including the predicted number of equivalent cycles at the next inspection time are used to predict the future condition. Though, any suitable inputs may be used to predict the future condition. Each of these input parameters may be described probabilistically as shown by plots 901-911 in FIG. 9A. Specifically, plots 901, 903, and 905 show example sketches of probability density functions for the estimated current condition, a; predicted operating conditions, σ; and predicted number of cycles at the next inspection time, $c_{t2}$. The equivalent representation, sketched in plots 907, 909, and 911, respectively, are cumulative distribution functions.

The probability distribution of the current condition, "a", may be determined in ways discussed, for example, in connection with step 517. The probability distribution of the predicted operating conditions, σ, may be predicted based on past operating conditions, actual operating conditions of components in the same pool, a schedule of operations for the component (or device), fleet history, expert analysis, or in any suitable way. The probability distribution of the predicted number of cycles at the next inspection time may be estimated from fleet history, expert analysis, a schedule of operation for the component (or device), or in any suitable way. Of course, if cycles may be measured directly and operation stopped for inspection after the desired number of cycles, it may be possible that there is little or no uncertainty in the number of cycles at the next inspection. But, typically the equivalent number of cycles, i.e., the cycles would be equivalent to a defined number of controlled loading cycles with an assumed spectrum, is not known with little or no uncertainty.

As illustrated the block diagram shown in FIG. 9B, the inputs, in this example a, σ, and $c_{t2}$, may be input to prediction module 248, which in turn uses a hyperlattice in condition progression database 245 to estimate the components condition at the next inspection time, $a_{t2}$. FIG. 9C shows a sketch of an example cumulative distribution function of $a_{t2}$.

The probability distribution of the predicted future condition may be determined by performing a series of look-ups in a hyperlattice stored by the condition progression database. In some embodiments, a rapid Monte Carlo method, or other such distribution estimation method, is used to predict the distribution function for the future condition from the hyperlattice by randomly selecting the input conditions in accordance with their respective distribution functions. In one embodiment, n values (e.g., n=100) are selected for each of the m inputs in accordance with the respective input's distribution function. The $n^m$ combinations are input to the hyperlattice to produce $n^m$ outputs. Though, the number of samples for each input may be chosen in any suitable way (e.g., independently). The output values describe the probability distribution of the output variable. The output values may be represented, for example, as a cumulative distribution function such as that shown in plot 913 (FIG. 9C). Though, the output values may be presented in any suitable way.

In some embodiments, the probability distribution of the future condition may be estimated by performing multiple look-ups in the hyperlattice where each look-up uses inputs from the distribution function of the current and possibly previous conditions of the component. The resulting outputs are weighted in accordance with the likelihood of the particular input conditions. In this way a probability distribution may be estimated for the future conditions.

In some embodiments, the cumulative distribution functions are divided into quantiles as illustrated for plot 907 in FIG. 9A. For example, each of the m inputs, the respective cumulative distribution function may be divided into n quantiles (e.g., n=100). As above the $n^m$ combinations are input to the hyperlattice to produce $n^m$ outputs which thus represent the probability distribution of the output variable.

It should be appreciated that the future condition may be performed for each indication separately on a component, or the future condition may be estimated for the entire component. That is, the future condition of the component may be determined by predicting the future condition of each indication, or the future condition of the component may be estimated taking in account the culmination of indications on the component.

Although, the individual confidence level in the current and/or previous component condition estimates may be below usual POD and PFA rates, the trend of the condition estimates may provide a reliable basis for estimating future states.

Figure 10A:
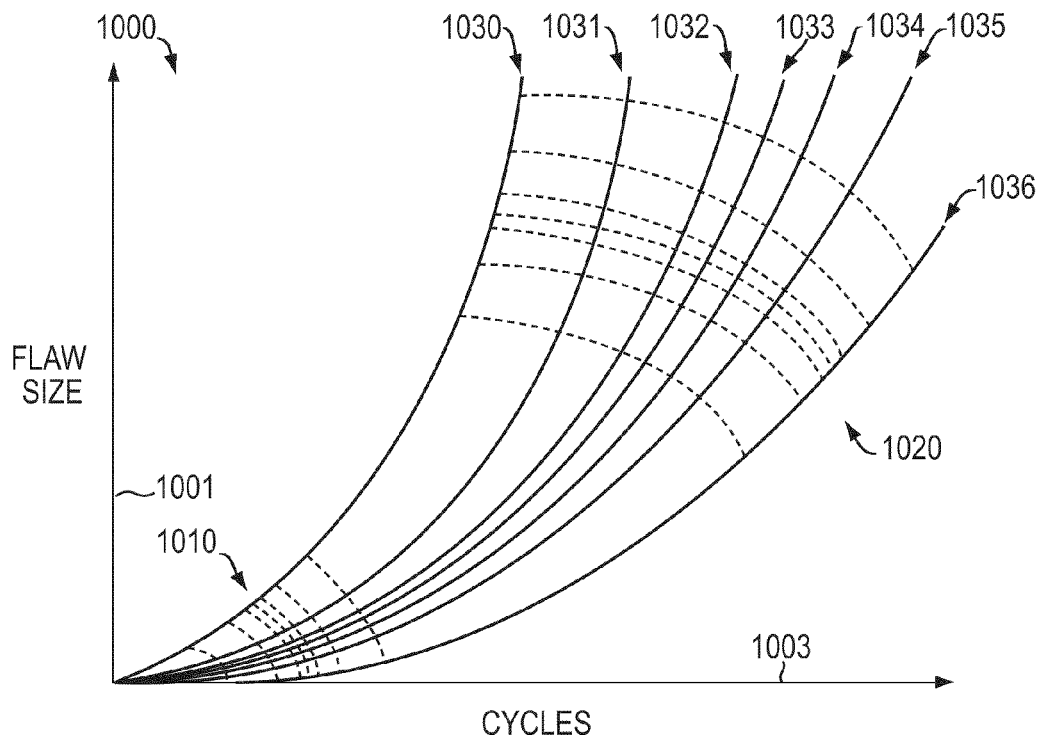
FIG. 10A is a sketch of a representation of a portion of a hyperlattice space according to some embodiments.

Plot 1000, shown in FIG. 10A, illustrates an operation that may be performed for the hyperlattice lookup. Specifically, plot 1000 shows the progressive growth of a flaw (axis 1001) as a function of the number of cycles (axis 1003) the component was used. The relationship between flaw growth and usage cycles is predicted for different operating conditions. The current condition of the component is generally referenced by area 1010 of plot 1000. The solid lines 1030-1036 represent paths of constant operating conditions for the component. The lines represent equal probability quantiles. The dashed lines in area 1010 and area 1020 also represent quantiles for the current and future condition, respectively. It should be appreciated that the smaller the simplex, the higher the probability the condition falls at that approximate simplex value. In some embodiments, identifying the future condition comprises identifying the smallest simplex. While plot 1000 illustrates a two dimensional hyperlattice, it should be appreciated that use of quantiles to divide grids and identify high probability outcomes via the smallest simplexes may be extended to higher dimensional hyperlattices.

Figure 10B:
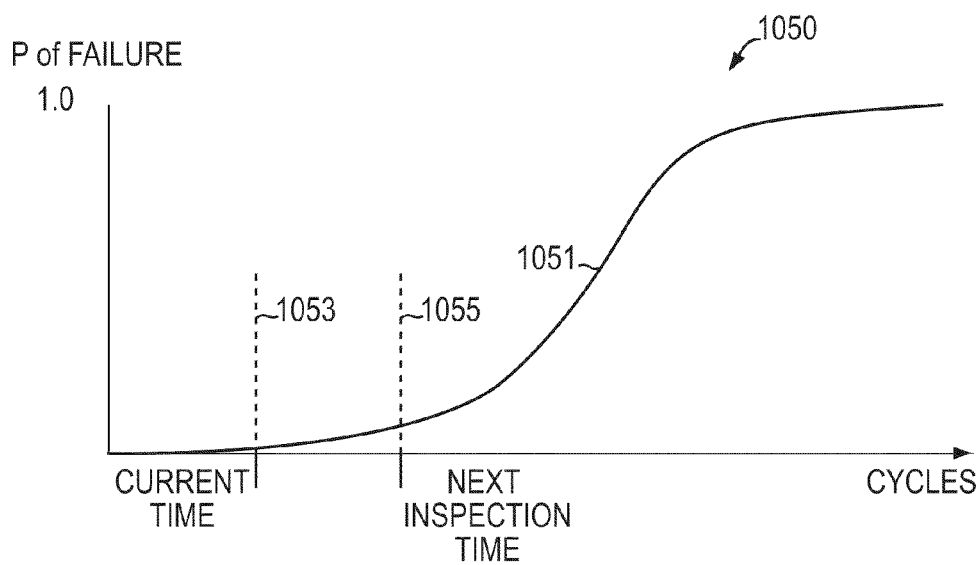
FIG. 10B is a sketch illustrating a representation of the risk of failure according to some embodiments.

In some embodiments, the probability distribution function of the future condition is displayed on a screen for a user to review. In some embodiments, the display is similar to plot 1000. Though, any suitable representation of the future condition may be shown. Additionally, the probability of failure may be displayed, for example, as show in plot 1050 of FIG. 10B. Specifically, plot 1050 shows curve 1051 which is the probability of failure as a function of the number of cycles. The current time 1053 and next inspection time 1055 may also be indicated. Though, any suitable representation of the probability of failure may be used.

After predicting the future condition, at step 521, an action is recommended based on the available information about the component, such as the estimated current condition and predicted future condition. Though, in some embodiments, the determination at step 521 may be based only on current and previous conditions (step 519 omitted). For example, a threshold flaw size may be set and if exceeded by the current condition a CBM action is performed (step 523) or the component is retired (step 527).

In some embodiments, the action is determined based on the risk of failure before the next inspection. For example, if the risk of failure is below a first damage tolerance limit, say 0.0001% risk of failure before the next inspection, the component may be allowed (method 500 continues to step 525). If the risk of failure is above the first damage tolerance limit, but below a second damage tolerance limit, say 0.0005%, the component may be repaired using a CBM action. If the risk of failure is above the second damage tolerance limit, the component may be retired. In some embodiments, the accept/reject/repair decision is based on the risk of failure before the next inspection or a combination of the crack size distribution estimated for the current time and the projected risk of failure before the next inspection. In some embodiments, the decision is based on the statistical risk for individual components. In another embodiment, the decision is based on the risk of failure for a fleet of components based on either 100 percent inspection of each component, or inspection of a subpopulation of such components. While yet another embodiment, the crack depth may determine whether a CBM action may be allowed along with associated risks.

If it is determined at step 521, that a condition based maintenance (CBM) action should be taken, method 500 continues to step 523. At step 523 a suitable CBM action is taken. After completing the CBM action, method 500 may return, for example, to step 517 to re-estimate the current condition of the component, predict its future condition, and determine whether the CBM achieved the desired affect.

If it is determined to accept the component as is, method 500 continues to step 525, at which the next inspection time is set. The next inspection time may be set, for example, in ways similar to those discussed in connection with step 505. Though, the additional information obtained through the subsequent inspections may enable the condition of the component to be projected more accurately.

If it is determined to reject the component, method 500 continues to step 527. At step 527 the component is retired and method 500 ends.

In some embodiments of method 500, inspection data may be obtained at the time of inspection (e.g., steps 501, 511) with a load, such as mechanical or thermal loads, intentionally applied to the component. For example, a composite propeller might be inspected with a high-resolution MWM-array with and without a controlled applied load, at two or more different inspection times. The inspection data at each inspection time may be subtracted for the two different loads (i.e., high load image minus low load image) and then differenced again in time to obtain an image of the change in the load difference images associated with impact events. The change in the images may be used as an input for searching the hyperlattice and predicting a future condition of the component and the uncertainty associated with that condition.

Though method 500 has been described for time sequenced inspection data, it should be appreciated that inspection data may be sequenced in any other suitable way.

While method 500 has been described for a manufactured component, it should be appreciated that the method may be applied to components for which manufacturing data is inappropriate or unavailable. For example, a local medical condition, such as a tumor or the bond integrity for a repaired joint, may be inspected at an initial time. A subsequent inspection may use the initial inspection as a baseline.

The inventors have further recognized and appreciated that the phenomenological models used to generate hyperlattices may be used for estimation of not only future condition but also the previous condition of a component. This may be useful when the data has been censored. That it, there are gaps in the historical record for a component's life. Censored data may exist, for example due to data loss.

Further, properties of the component at the time of manufacturing may be estimated by determining what initial conditions would lead to the observed current condition of the component. Such root cause information may be useful for determining, for example, material properties at the time of manufacturing that may only be investigated through expensive or destructive testing techniques. Accordingly, the framework may be used to estimate missing data or determine the root cause of the current conditions.

Figure 11:
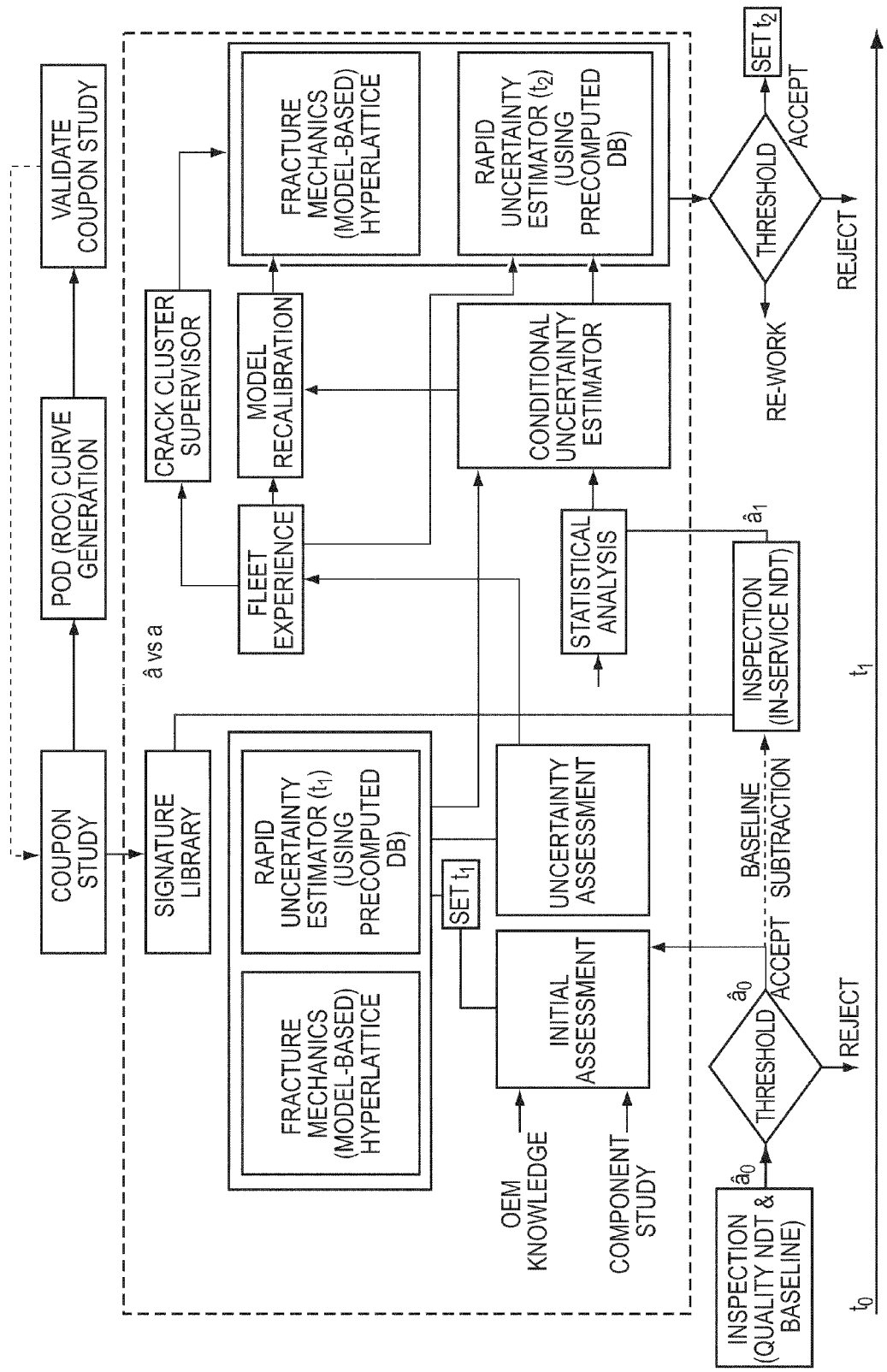
FIG. 11 is a flow diagram of a method for adaptively managing the life of a component according to some embodiments.

FIG. 11 shows a flow diagram of a method for adaptively managing the life of a component according to some embodiments.

A graphical user interface (GUI) that may serve as a front end for method 500 (FIGS. 5A-5B) is presented with reference to FIGS. 12A-13J. Though, it should be appreciated that any suitable user interface may be used. Further, it should be appreciated that in some embodiments, method 500 is automated and may not require regular interaction with an operator.

The GUI provides an environment for component adaptive life management (CALM). For the purposes of illustrating the CALM environment GUI, an example of a metal component that develops cracks is discussed. Though, the CALM environment may be used for any suitable type of component or flaw type, or a process other than damage evolution such as heat treatment, forming, machining, curing, welding, or a medical procedure progression.

According to some embodiments, the CALM environment is implemented by one or more modules. The modules that are used during inspection of a component may be implemented to operate within a data acquisition and processing application such as the GridStation™ environment available from JENTEK Sensors Inc., Waltham, Mass. The modules may include a supervisor module that guides the operator through the process, and one or more plug-in modules that may implement, for example, data processing, statistical analysis, and automatic report generation.

According to some embodiments, there are several plug-ins that implement various stages of the data processing. A plug-in named "Find Indications" may be used at the baseline (t0) stage and it identifies the locations and magnitudes of indications based on changes in the measured material property, for example, a localized drop in conductivity.

A plug-in named "Find Indications 2" may be used at the t1 stage of the inspection process. Find Indications 2 finds indications after baseline subtraction of the baseline data taken at t0 and uses shape filtering, for example, using signatures from signature library 244 (FIG. 2).

A plug-in named "CALM CDF(a)" may be run after Find Indications 2. For each indication identified by the plug-in "Find Indications 2", CALM CDF(a) uses "â vs. a" statistical analysis to compute a cumulative distribution function for the crack size at this indication at time t1 (i.e., cdf(a)|t1). CALM CDF(a) then runs this CDF, together with CDFs on stress and usage cycles, through an appropriate hyperlattice in two separate ways: (1) generate cdf(a)|t2 that computes the expected crack size distribution at this location at a future time t2 given by the CDF(usage) provided; and (2) generate cdf(usage)|a2 that computes the probability distribution of usage cycles for the crack at this location to grow to a predetermined threshold size.

A "Reporting" plug-in may be used to automatically generate reports based on the outputs from the other plug-ins.

The supervisor module may generate the GUI and other visual elements of the software environment encountered during an inspection. An operator will begin with the window 1200 shown in FIG. 12A. Here there are three links to choose between, depending on whether this is a baseline scan (t0), a first inspection scan (t1), or a subsequent inspection scan (t2+).

Figure 12A:
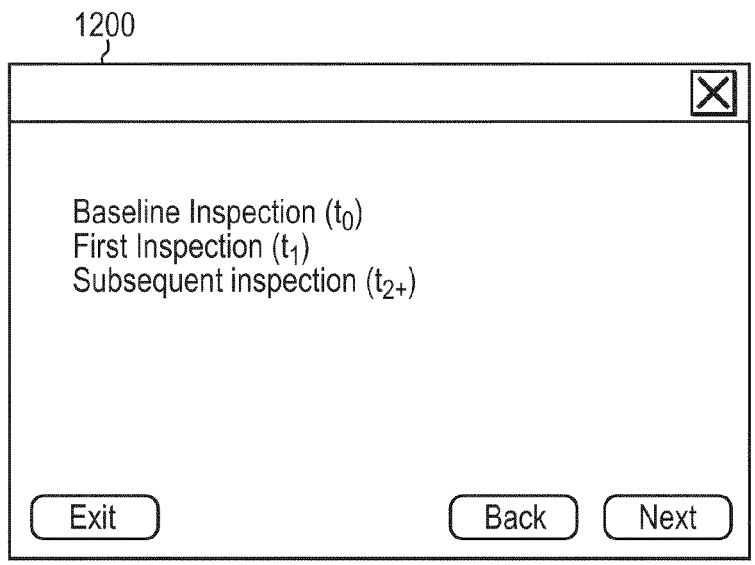
FIG. 12A-12Z show a graphical user interface for controlling adaptive life management according to some embodiments.
Figure 12B:
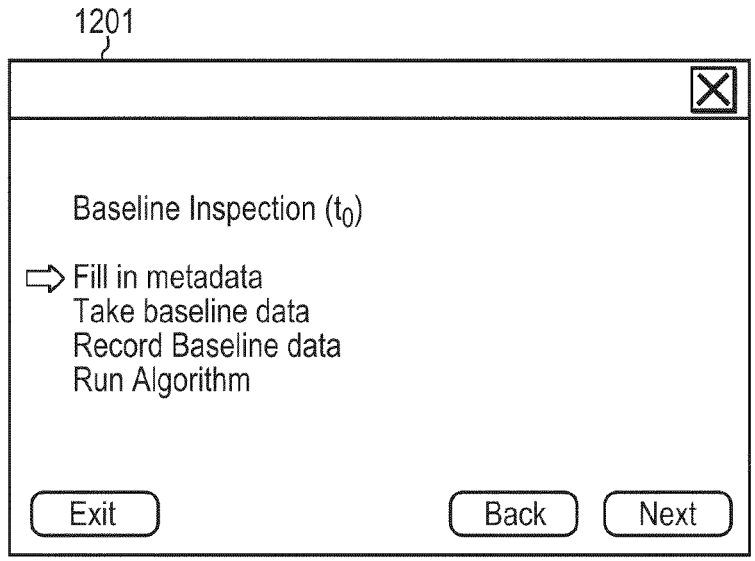

If the operator clicks on the Baseline Inspection link in window 1200, he is shown the steps that to be completed in a baseline inspection, as shown in window 1201, FIG. 12B. The next step is shown in bold and with a yellow arrow. This is the step that will also be reached by clicking on the "Next" button.

Figure 12C:
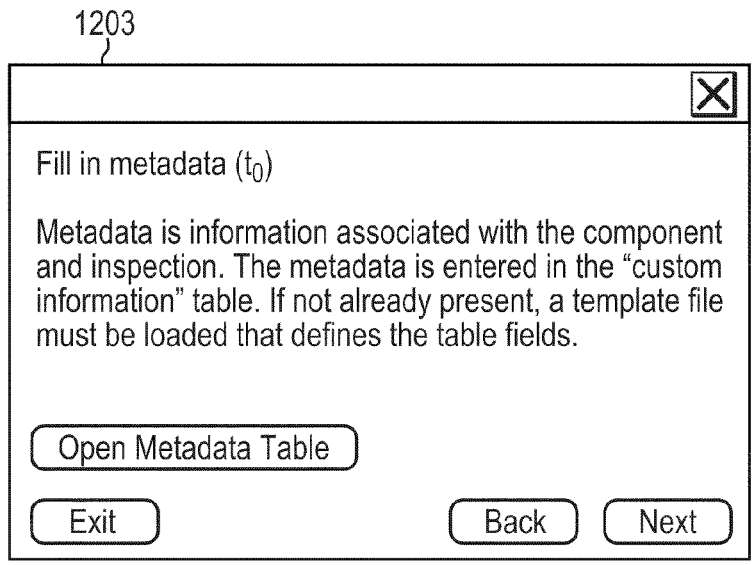

In this step the operator is asked to fill in component metadata, as shown in window 1203, FIG. 12C. If the operator clicks on the purple action button, the metadata table in GridStation opens (unless already open). An example of metadata in shown in table 1205, FIG. 12D. The operator may fill out the second column of table 1205. The fields in this table may be customizable. The metadata in table 1205 may be saved with any data acquired as part of the inspection and is also included in the automatically generated reports.

After the operator fills out the metadata table, he is taken back to the list of steps, as shown in window 1207, FIG. 12E.

The next step in the procedure is to acquire the baseline scan data on the component. The supervisor provides the operator with a set of instructions, as shown in window 1209, FIG. 12F.

Figure 12G:
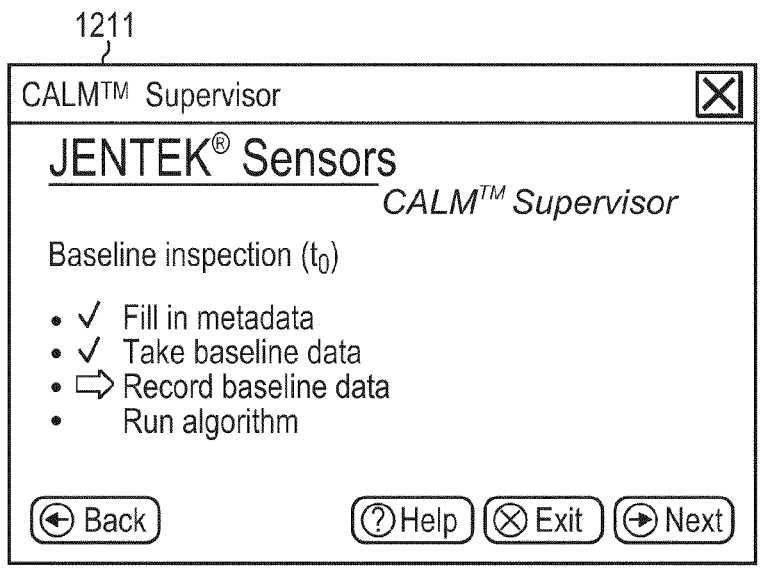
Figure 12H:
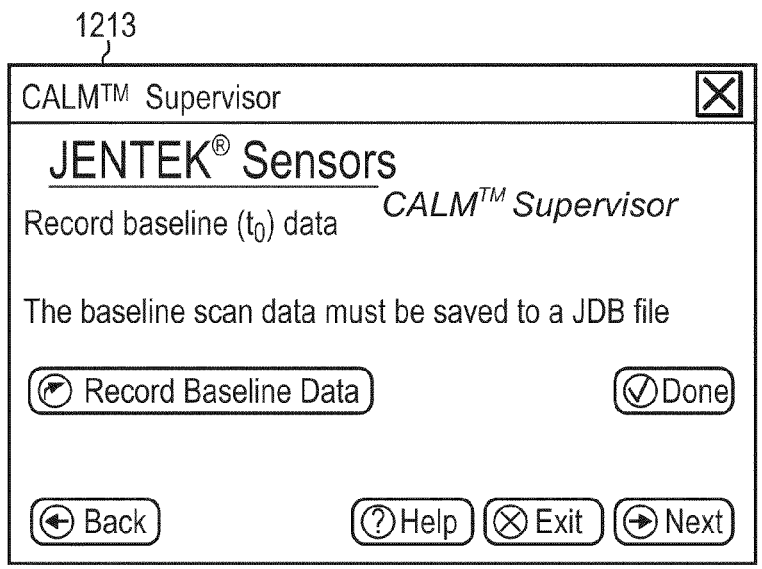

After the scan data is acquired, the operator is instructed to save the data, as shown in windows 1211 and 1213 of FIG. 12G and FIG. 12H, respectively. When the operator clicks on the "Record baseline data" in window 1213, he is presented with a dialog to save the baseline data.

Figure 12I:
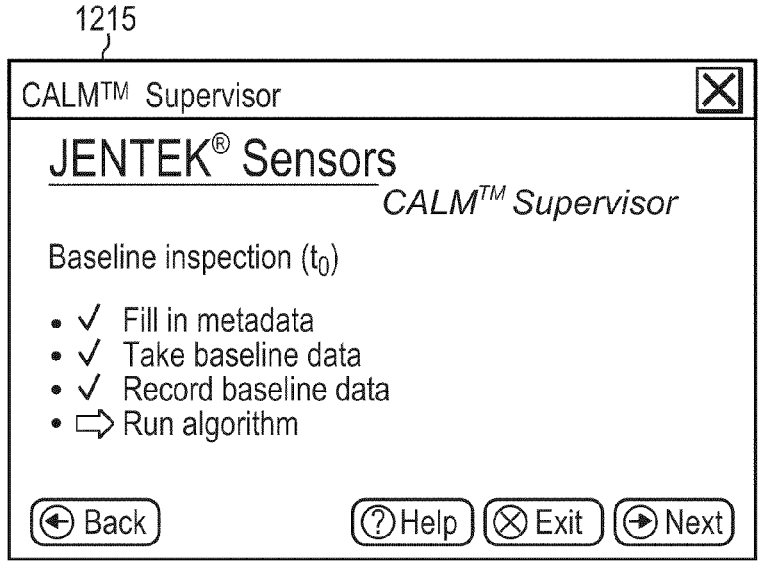
Figure 12J:
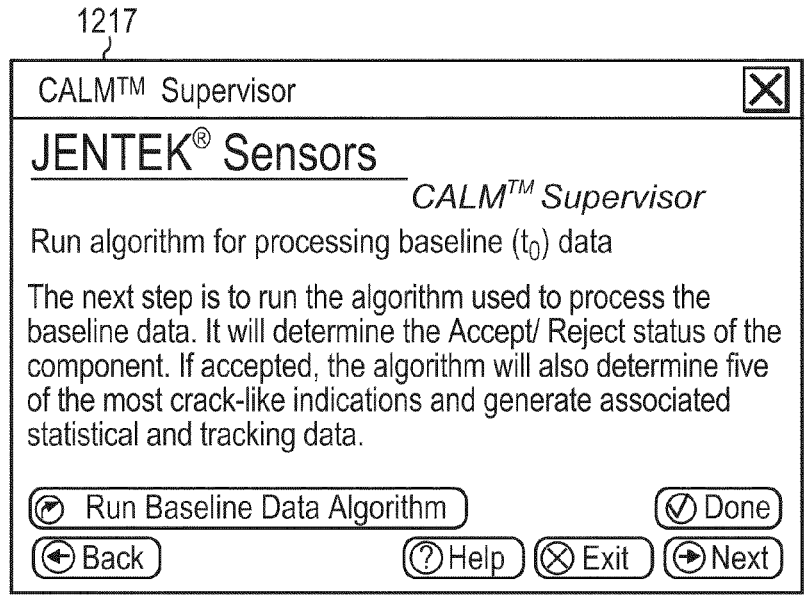
Figure 12K:
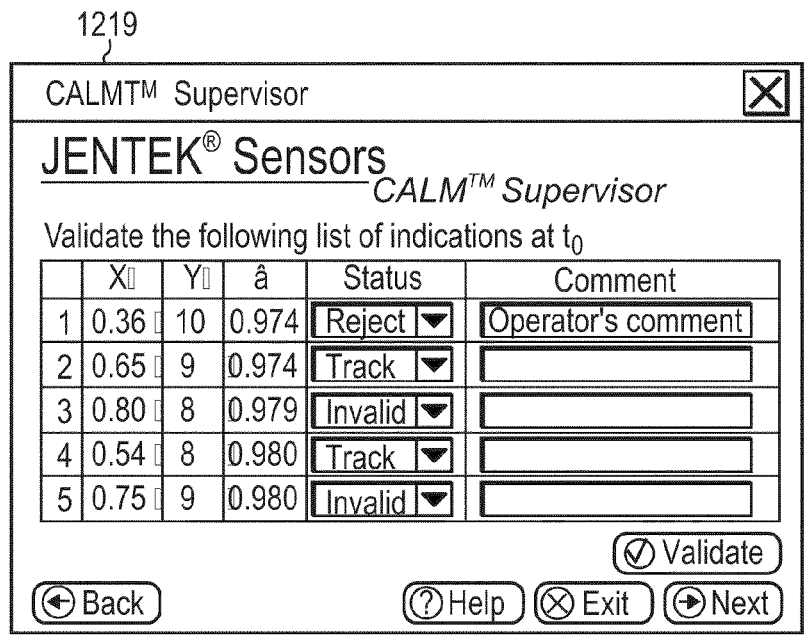

After the data has been acquired and saved, it is time to run the baseline indications algorithm (the plug-in named "Find Indications") as shown in window 1215, FIG. 12I and window 1217, FIG. 12J. The algorithm begins data processing after the operator clicks on the "Run Baseline data algorithm" shown in window 1217.

Figure 12L:
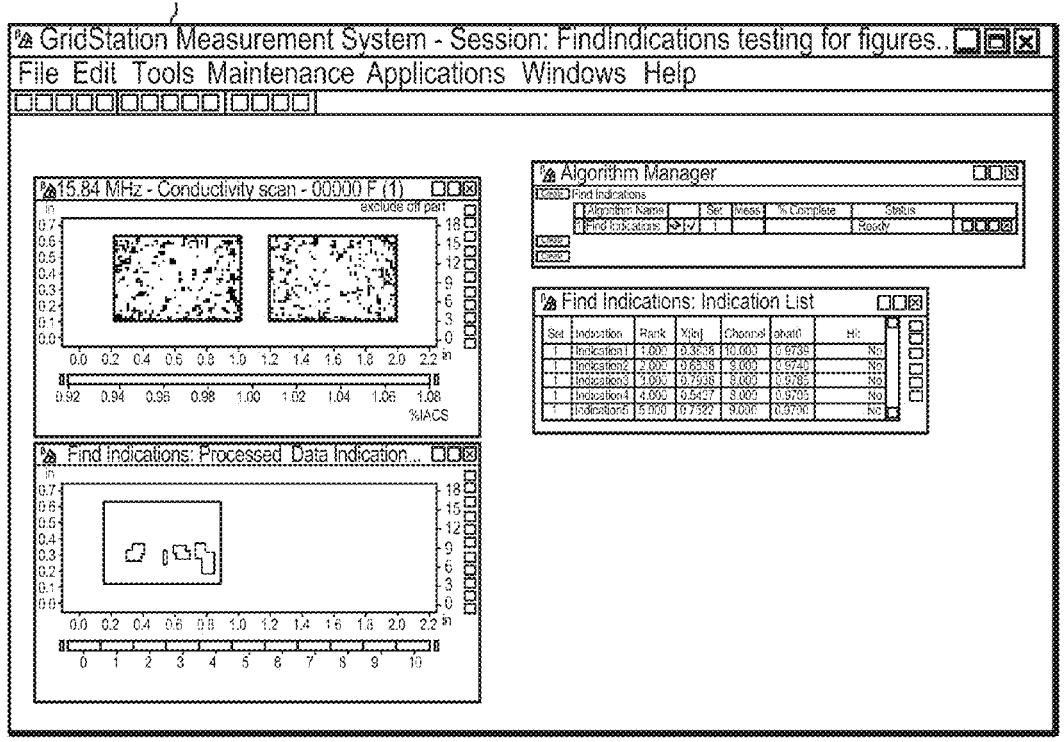

After the plug-in has finished executing, the data is presented in visual form as C-scans, as shown in the screen-dump in window 1221, FIG. 12L. These C-scan images may also be included in the automatically generated report. In window 1223, FIG. 12M, the operator is presented with a table that shows a list the most likely indications, as determined by the Find Indications module. This is shown in window 1219, FIG. 12K. The table lists the physical location of the indications, the magnitudes (a), and the status. The status may be either "Reject" or "Track", based on whether the indication is above a certain threshold that may be specified as part of the plug-in configuration and included in the automatically generated reports. In window 1219, the operator has the opportunity to change the status of the indications, or to set the status to "Invalid" which is used to let the environment know that this indication should not be retained for further tracking. The operator can also enter comments for each indication, which are retained with the data. After this the operator is asked to validate the list of indications by clicking on the "Validate button".

Figure 12M:
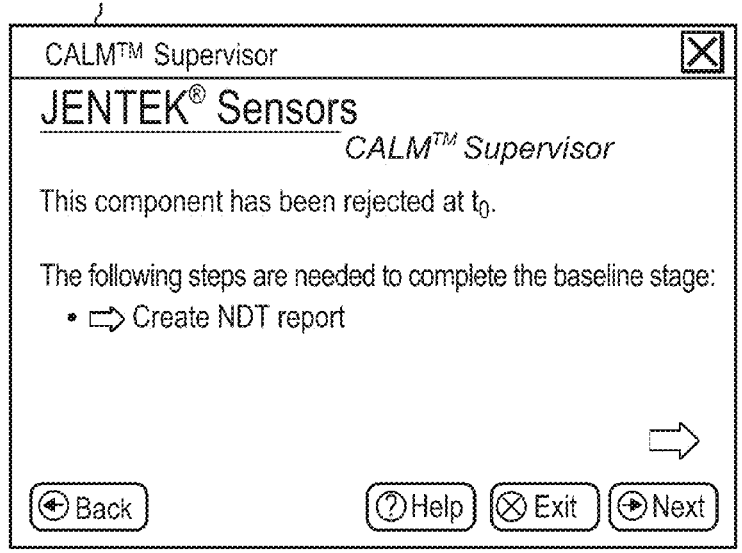
Figure 12N:
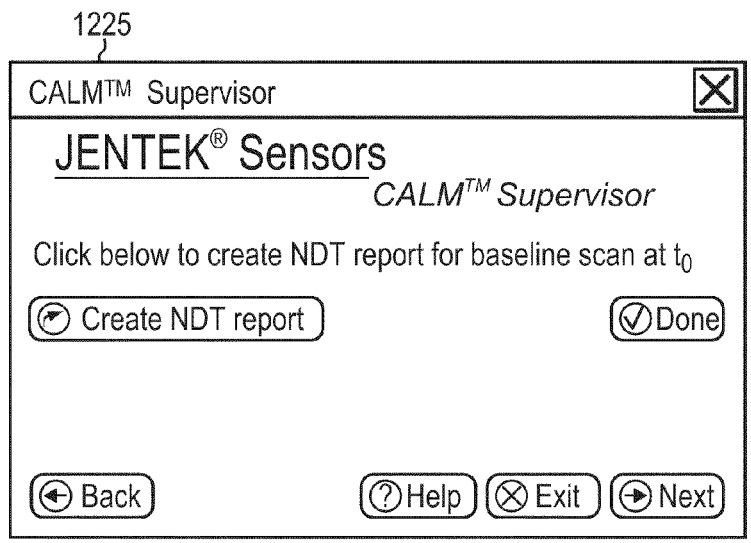

If the status of any of the indications in the table in window 1219 are "Reject" after validation by the operator, then the supervisor module informs the operator that the component has been rejected and prompts him to create an NDT report, as shown in windows 1223 and 1225, FIG. 12M and FIG. 12N, respectively. If this is the case, this completes the inspection of this component and the operator is shown the screen in window 1238, FIG. 12R.

Figure 12O:
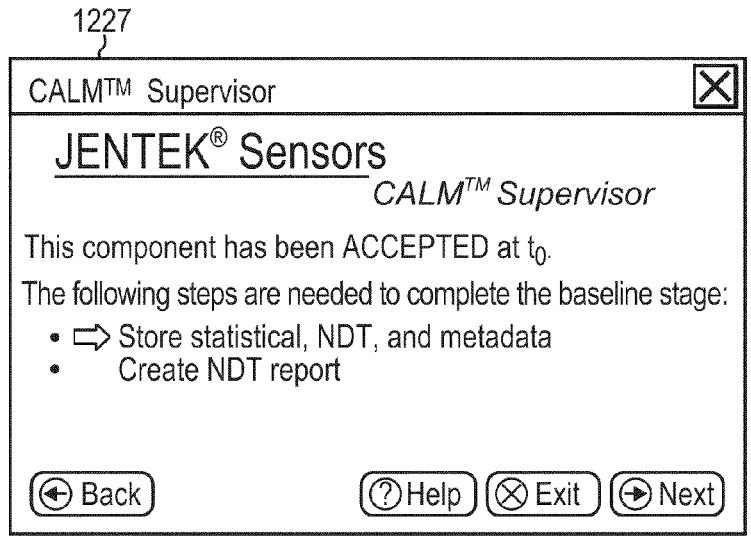
Figure 12P:
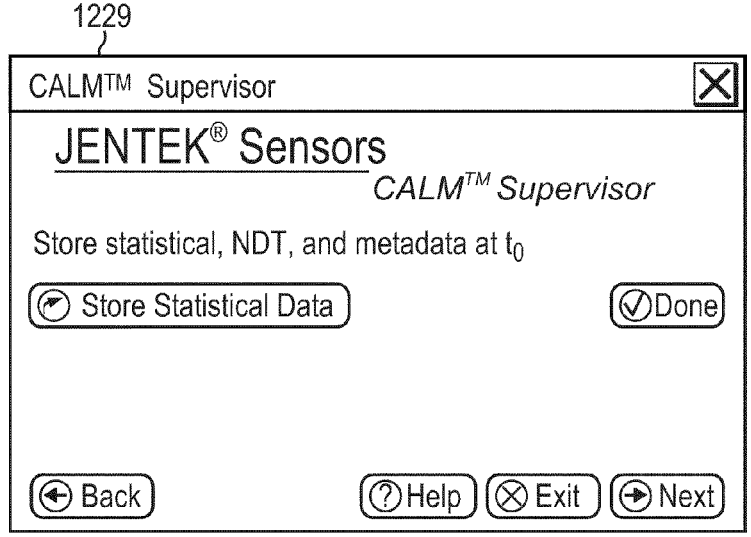
Figure 12Q:
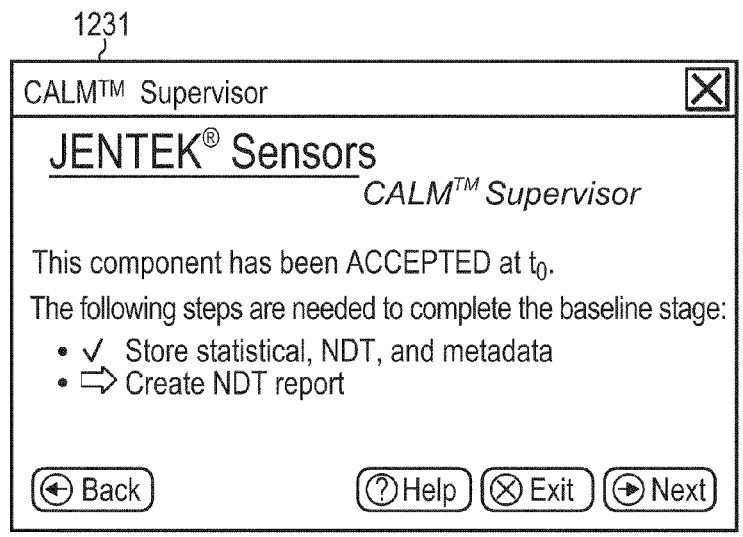
Figure 12R:
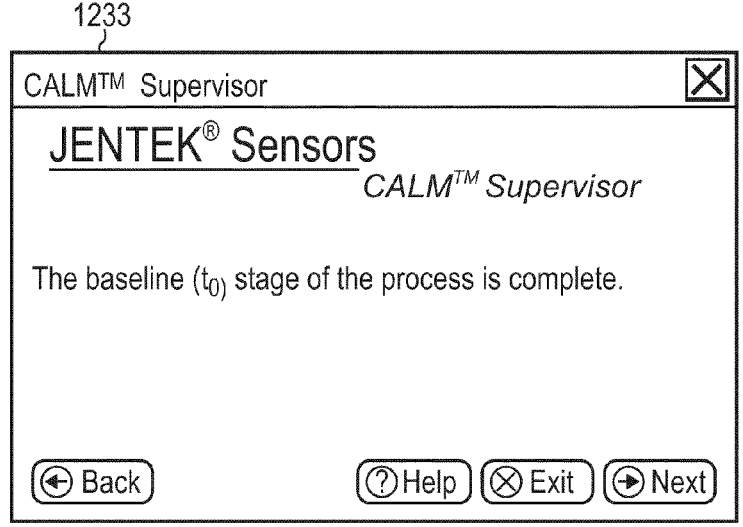

If, on the other hand, none of the indications have a "Reject" status, the operator is given the next set of steps, as shown in window 1227, FIG. 12O. These steps include saving the results of the data analysis for future inspections (window 1229, FIG. 12P) and generating an NDT report (window 1231, FIG. 12Q). After these steps are completed the baseline scan stage of the inspection is complete and the operator is shown the screen in window 1238, FIG. 12R.

Clicking on "Create NDT report" button in window 1227 (FIG. 12O) runs the reporting plug-in which automatically generates an appropriate report.

Figure 12S:
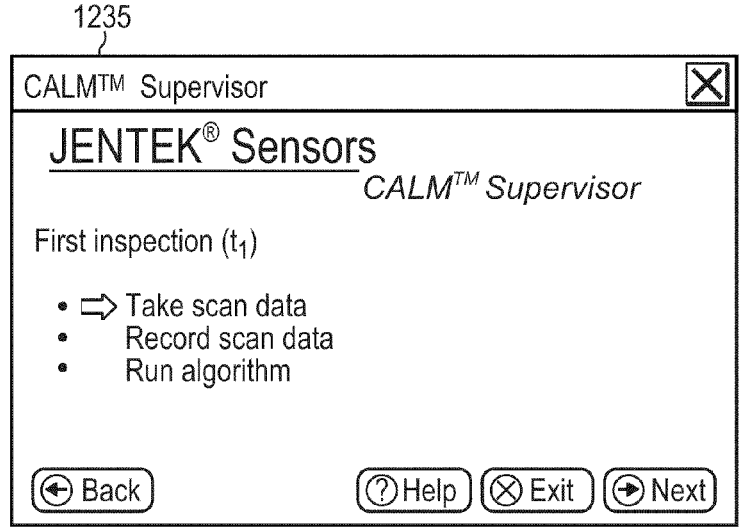
Figure 12T:
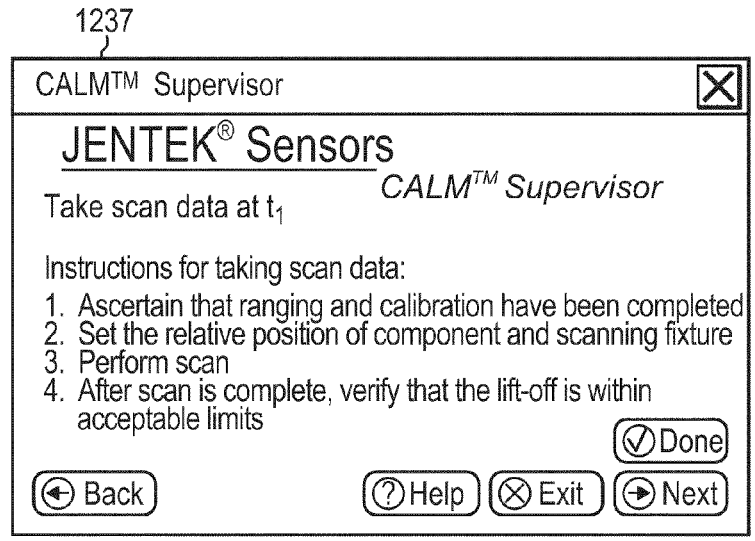
Figure 12U:
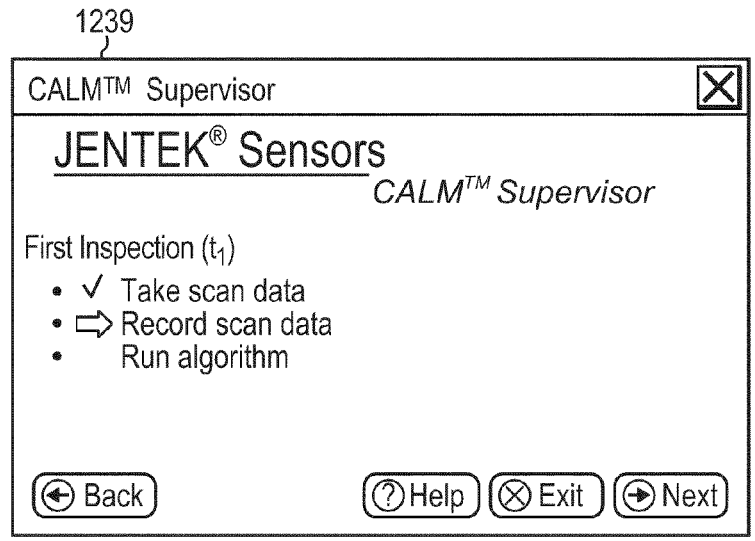
Figure 12V:
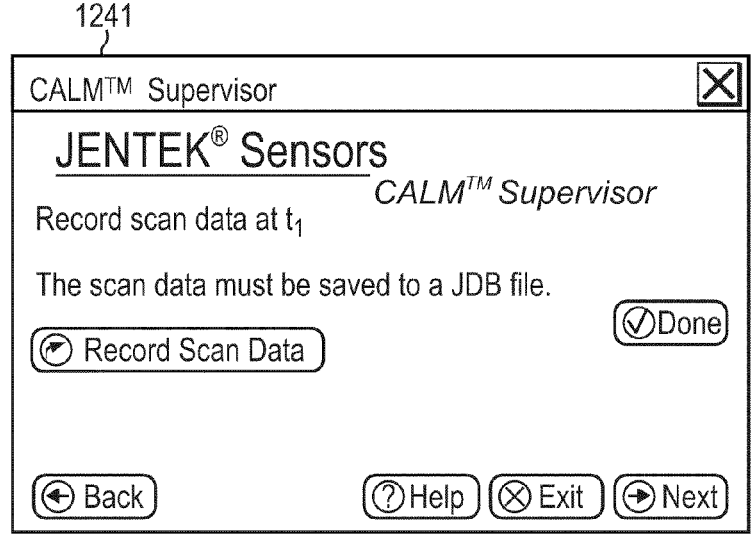

After the operator clicks on the First Inspection (t1) link in window 1201, FIG. 12A, he is shown the steps that must be completed in an inspection at time t1, assuming that data from a baseline scan is available, as shown in window 1235, FIG. 12S.

In this case no metadata is required of the operator, because it was already filled out at the time of the baseline scan. The operator is, however, always able to edit the data in the metadata table and the edited date will be saved in future data files and included in automatically generated reports.

Windows 1237, 1239 and 1241 (FIGS. 12T-12V) walk the operator though the steps to take a scan on the component and store the scan data. These steps are similar to the steps in the baseline stage, described previously.

Figure 12W:
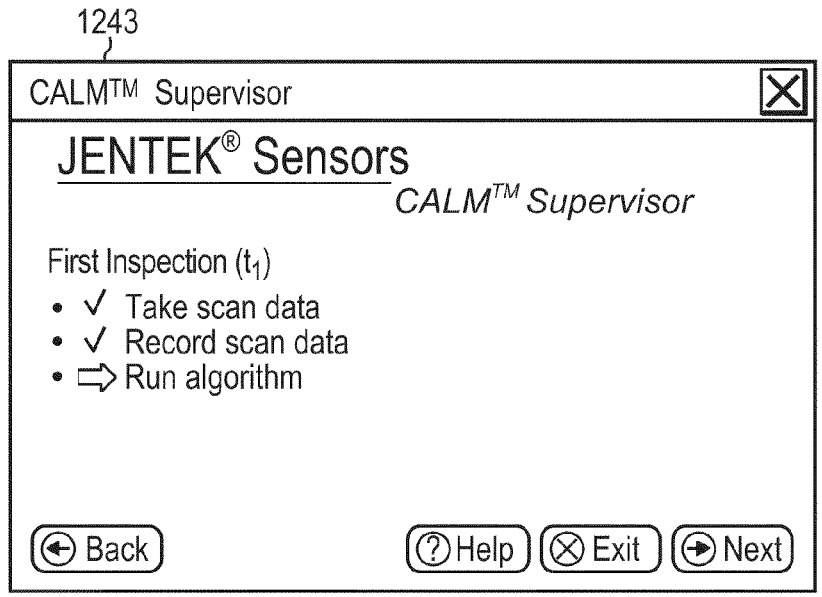
Figure 12X:
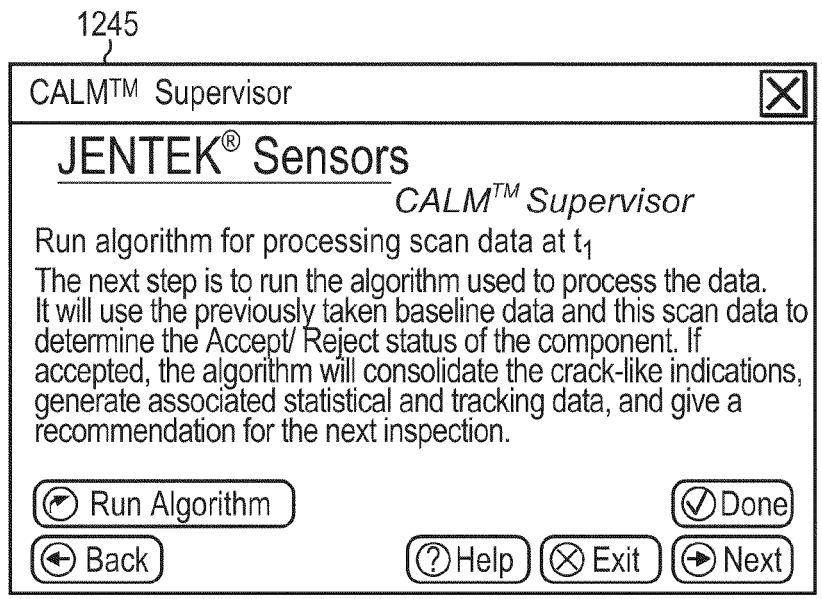

After the data has been acquired and saved, it is time to run the data processing and statistical algorithms (the plug-ins named "Find Indications 2" and "CALM CDF(a)") as shown in windows 1243 and 1245 of FIG. 12W and FIG. 12X, respectively. The algorithms begin data processing after the operator clicks on the "Run Algorithm" button shown in window 1245, FIG. 12X.

Figure 12Y:
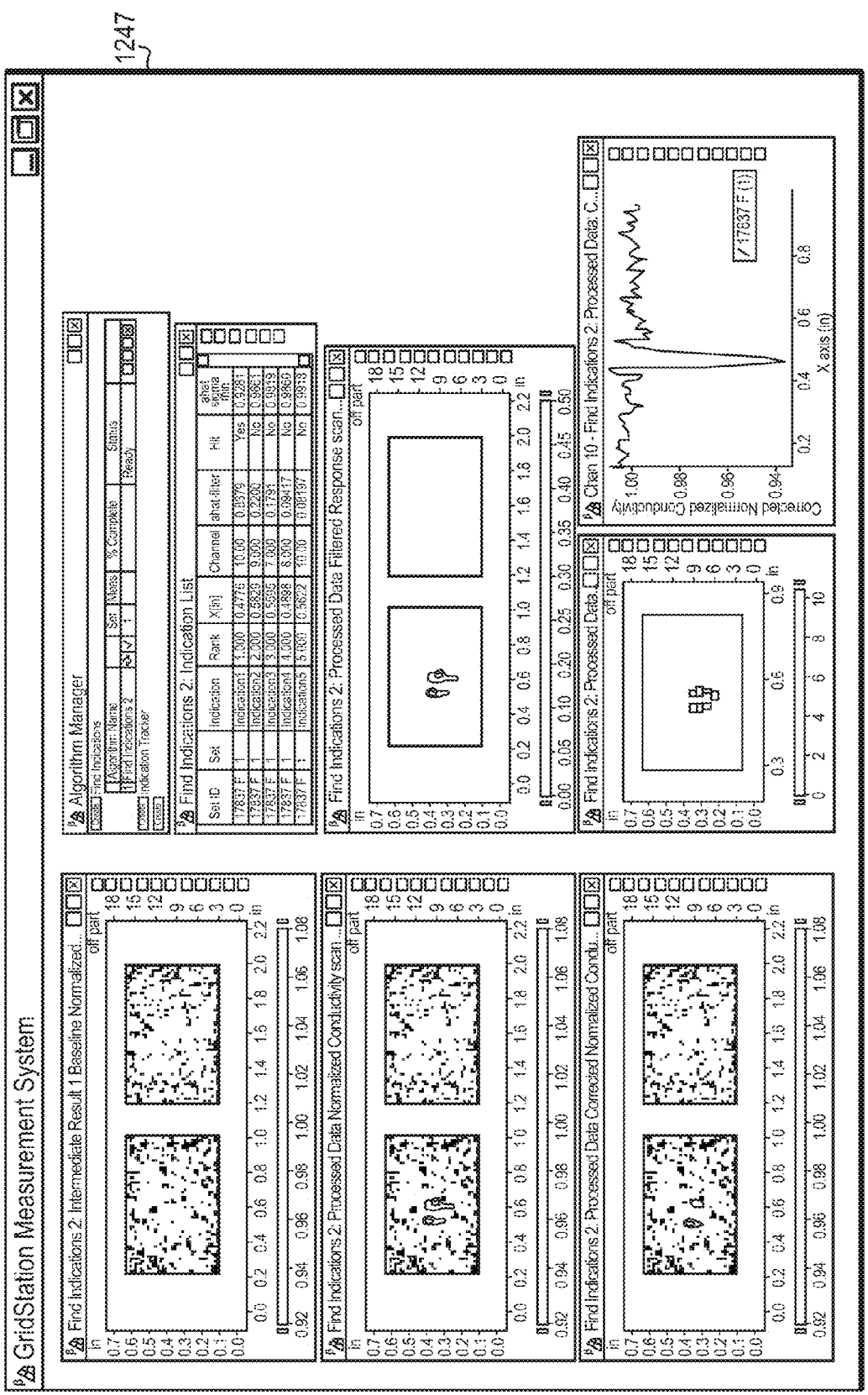
Figure 12Z:
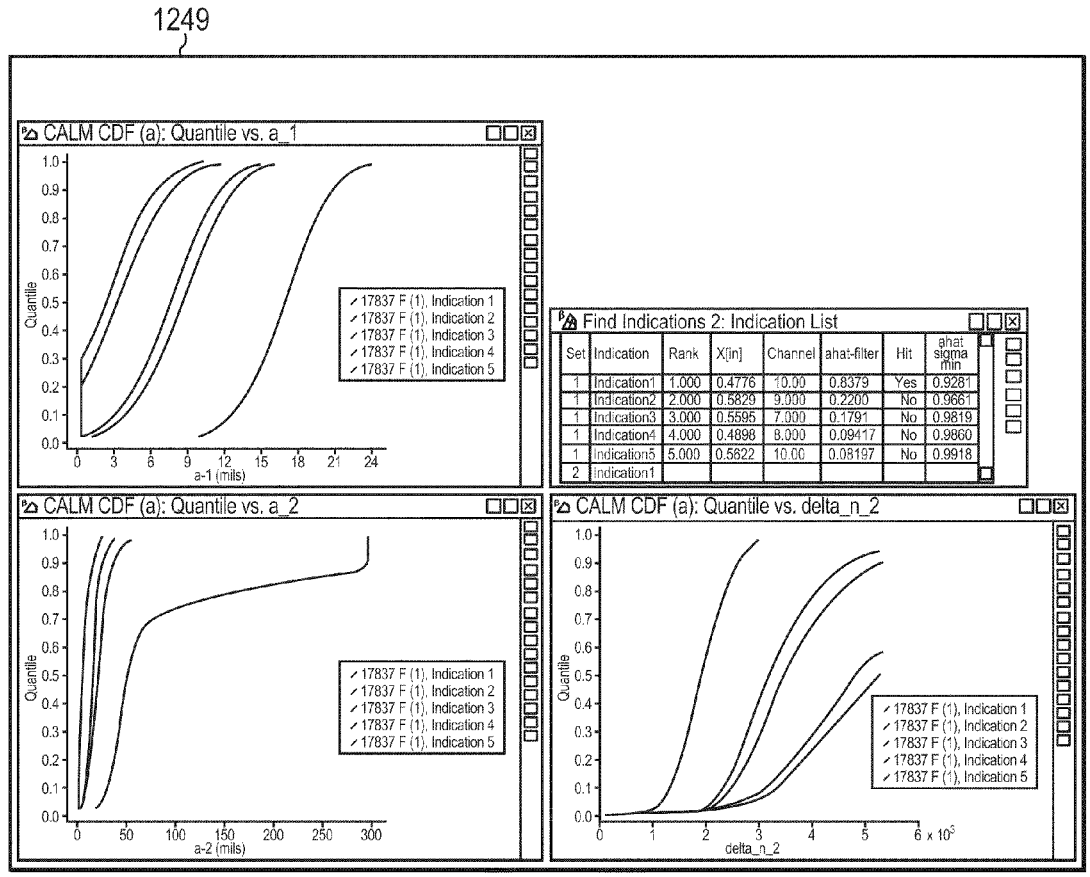

After the plug-ins have finished executing, the data may be presented in visual form as C-scans and statistical CDF function curves, as shown in the screen-dumps in window 1247, FIG. 12Y and window 1249, FIG. 12Z. Note that for clarity in these figures some of the windows have been hidden (including the supervisor window) so that the data views can be shown. These C-scan and graph images may also be included in the automatically generated report. Within the supervisor window, the operator is presented with a table that shows a list of the top five most likely indications, as determined by the algorithm. This is shown in window 1301, FIG. 13A. The table lists the physical location of the indications, the magnitudes (a), and the status. The status can be either "Reject" or "Track", based on whether the indication is above a certain threshold, specified as part of the plug-in configuration and included in the NDT reports. In the screen shown in window 1301, the operator has the opportunity to change the status of the indications, or to set the status to "Invalid" which is used to let the software know that this indication is not "real" and should not be retained for further tracking. The operator can also enter comments for each indication, which are retained with the data. After this the operator is asked to validate the list of indications by clicking on the "Validate button".

Figure 13A:
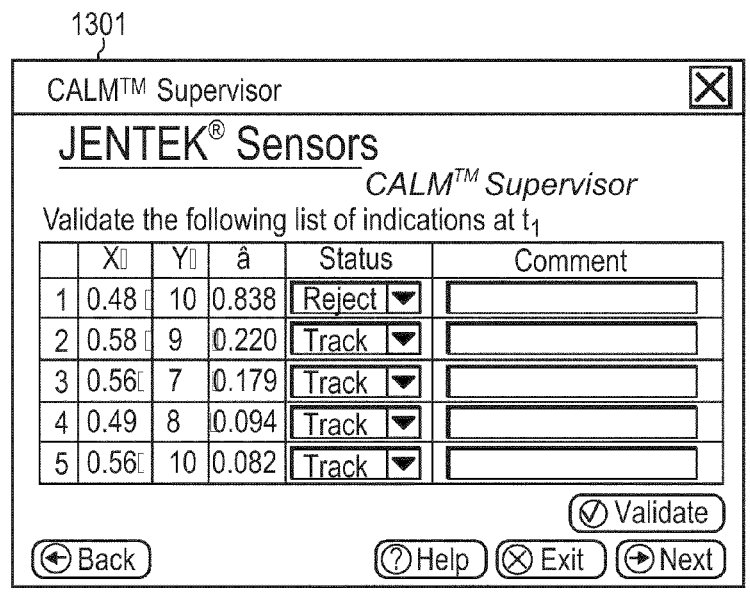
FIG. 13A-13J show a graphical user interface for controlling adaptive life management according to some embodiments.
Figure 13B:
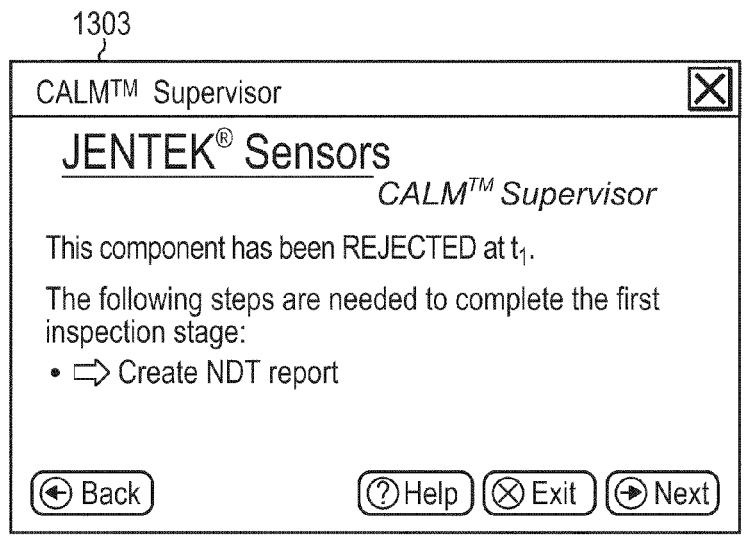
Figure 13C:
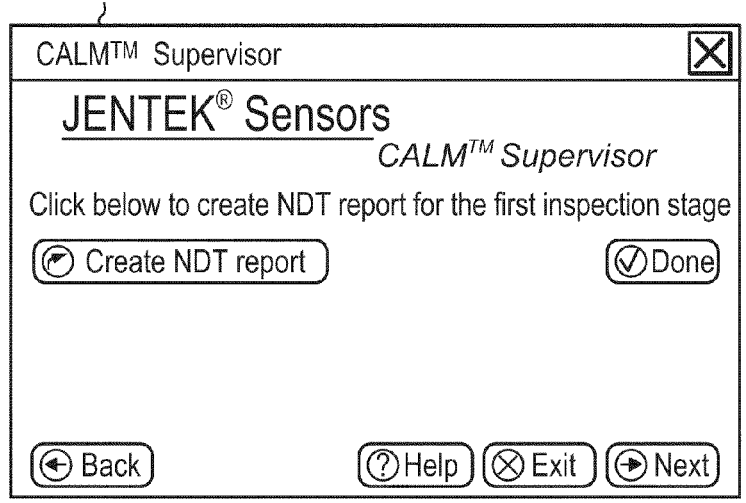

If the status of any of the indications in the table in window 1301 are "Reject" after validation by the operator, then the supervisor informs the operator that the component has been rejected and prompts him to create an NDT report, as shown in window 1303, FIG. 13B and window 1305, FIG. 13C. If this is the case, this completes the inspection of this component and the operator is shown the screen in window 1317, FIG. 13I.

Figure 13D:
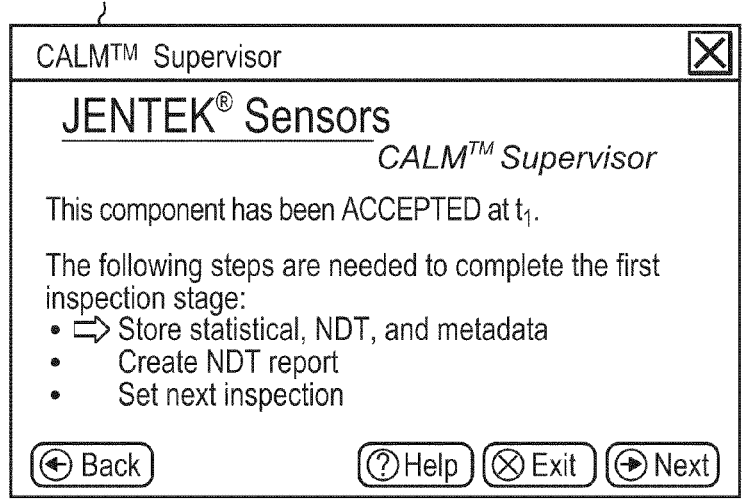
Figure 13E:
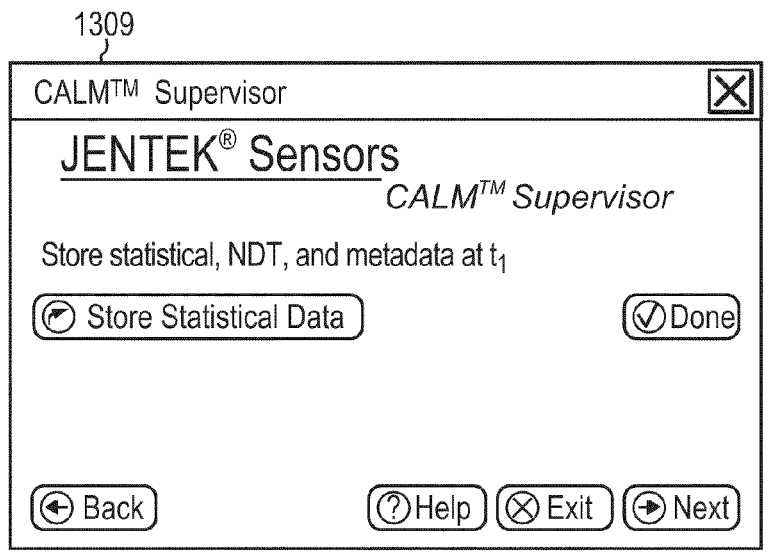
Figure 13F:
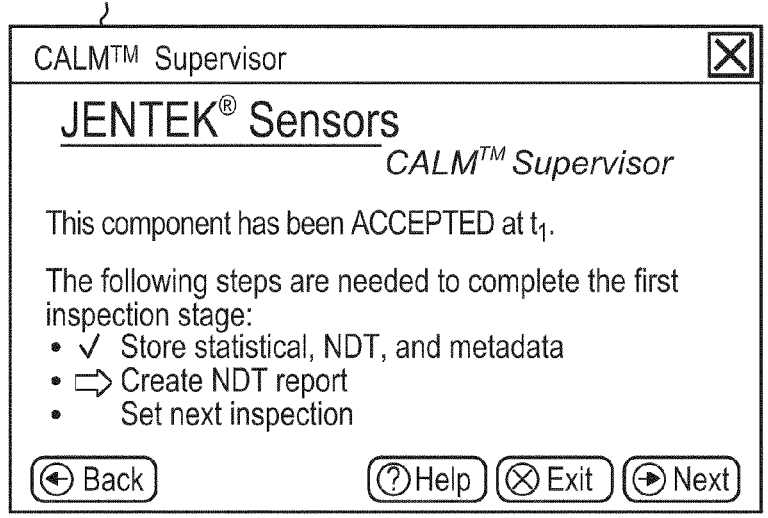
Figure 13G:
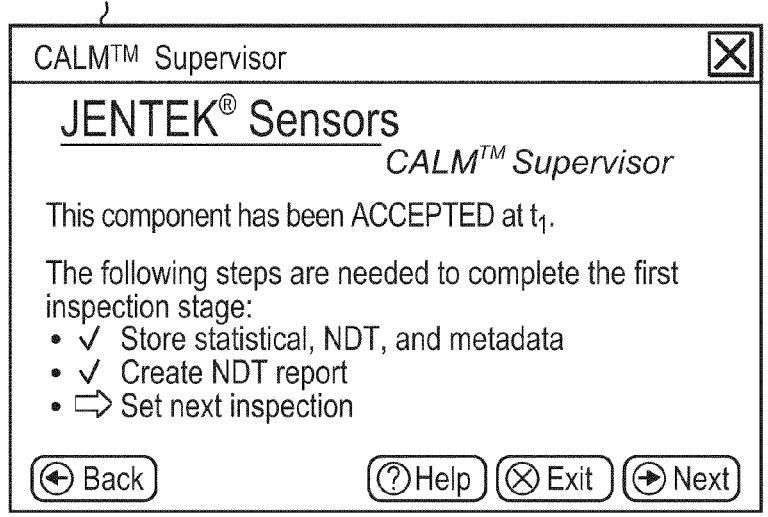

If, on the other hand, none of the indications have a "Reject" status, the operator is given the next set of steps, as shown in window 1307, FIG. 13D. These steps include saving the results of the data analysis for future inspections (window 1307, FIG. 13D and window 1309, FIG. 13E), generating an NDT report (window 1305, FIG. 13C), and setting the next inspection interval based on the statistical analysis through the fuzzy lattice.

Figure 13H:
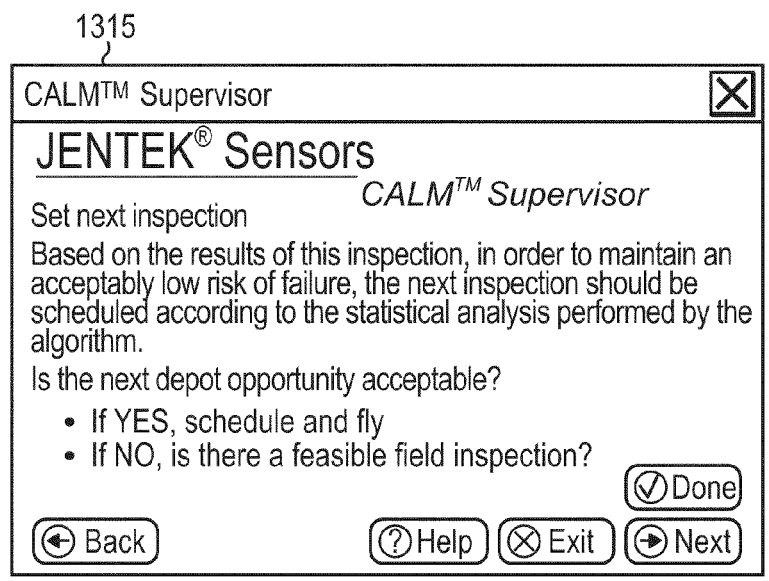
Figure 13I:
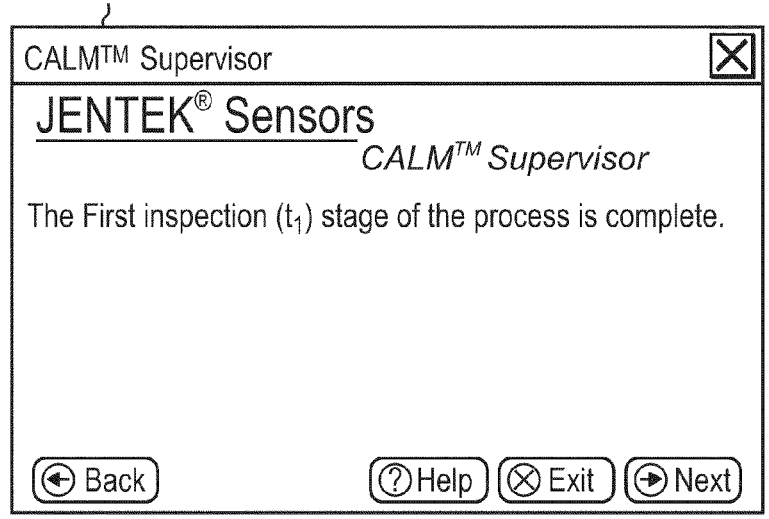
Figure 13J:
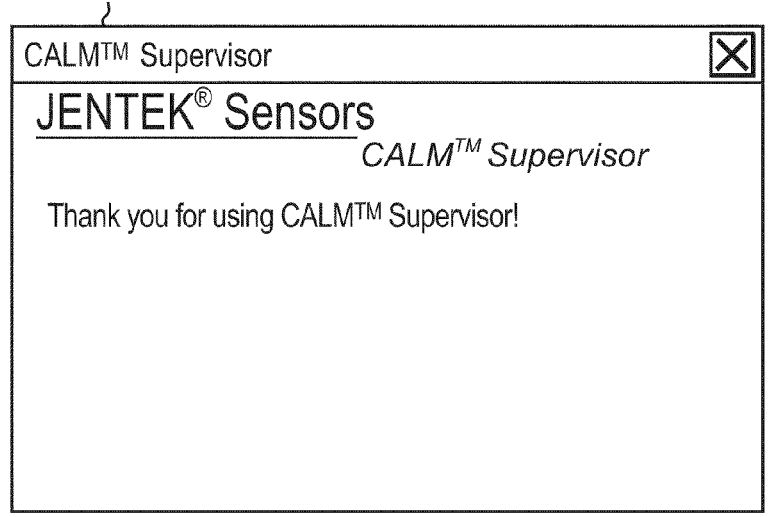

After these steps are completed the baseline scan stage of the inspection is complete and the operator is shown the screen in window 1317, FIG. 13I. After finishing work with the supervisor, the operator is instructed that the process is over (window 1319, FIG. 13J).

As already discussed, for each indication identified by the plug-in "Find Indications 2", the plugin "CALM CDF(a)" uses the "â vs. a" statistical analysis to compute a cdf(a)|t1 cumulative distribution function (CDF) for the crack size at this indication. This result is shown as a separate curve for each indication, as seen in window 1249, FIG. 12Z (upper left). This analysis uses â vs. a data gathered as part of this effort on Titanium alloy coupons and the statistical data that characterize this correlation are input as part of the plug-in configuration.

It then runs this CDF, together with CDFs on stress and usage, through the fuzzy lattice to generate cdf(a)|t2 that computes the expected crack size distribution at this location at a future time t2 given by the CDF(usage) provided. This result is shown in the curves in window 1249, FIG. 12Z (lower left). In the example presented here, the stress and usage input CDF distributions were assumed to be normal, with means and standard deviations as shown in the plug-in configuration, in this case set to 415±42 ksi and 2000±200 cycles respectively. The plug-in allows for non-normal distributions to be included as separate data files.

The plug-in also generates cdf(usage)|a2 that computes the probability distribution of usage cycles for the crack at this location to grow to a predetermined threshold crack size. This threshold crack size is part of the plug-in configuration, set to 79 mils (2 mm) in this example. The results of this analysis are shown in the curves in window 1249 of FIG. 12Z (lower right). This CDF(usage) distribution for the highest ranking indication (indication 1) is what is used to set the next inspection interval, as indicated in window 1315, FIG. 13H, given a tolerable risk level for failure before the next inspection.

Clicking on the "Create NDT report" button in window 1305, FIG. 13C runs the reporting plug-in which automatically generates a report such as a Word document.

Flaw Size Distribution Inferred From NDT Inspection Results

A mean relationship between NDT signal and flaw sizes is established utilizing coupon data. However, individual flaw signals will vary about that mean relationship. Thus, from a population of flaws of the same size a distribution of sensor measurement signals would be produced. Although from the same size flaw, if the mean relationship was used for each of those signals to estimate a corresponding flaw size, the resulting estimated flaw sizes would be distributed about the actual flaw size. The process developed and specified here may be used to quantify the resulting uncertainty in estimating flaw sizes that is induced by signal variation. Though, uncertainty may be quantified in any suitable way.

The general technique of quantifying probability of detection (POD) for an NDE process based on signal data is referred to as an "a-hat" versus "a" analysis. This nomenclature comes out of the first presenters of the methodology using the variable "a" to refer to flaw size with "a-hat" referring to the signal data. The methodology is that of regression in which the signal is related to the flaw size through some relationship. The most commonly used relationship is that that, on average, the logarithm of the signal has a linear relationship with the logarithm of the flaw size. That is, $$E[\ln(S)] = \beta_0 + \beta_1 \cdot \ln(a), \quad (1)$$

where S denotes the signal (often written â, thus the name a-hat) and E is the expectation operator.

Equation (1) is not enough to quantify the reliability associated with the NDE process, as it only models an average relationship of signal with flaw size. A full specification of the distribution of the signal may be modeled by adding an error term that captures the difference between the signal relationship and the mean line. That is, $$\ln(S) = \beta_0 + \beta_1 \cdot \ln(a) + \in, \quad (2)$$

where $\in$ is now a random variable with mean 0. The full probabilistic nature of the signal in this representation is captured in the mean $\beta_0 + \beta_1 \cdot \ln(a)$ and the distribution assigned to the zero mean random variable $\in$.

The assumption that $\in$ has a Gaussian distribution with mean 0 and variance $\delta^2$ is the usual basis of analysis that yields the equivalence of the maximum likelihood estimates (MLE) for $\beta_0$ and $\beta_1$ and the least squares estimates. Although the above model has served well to capture the behavior of many reliability characterizations, it is worth noting that the assumptions do not have to be restricted to those given above. The problem may be generalized to $$g_S(S) = \beta_0 + \beta_1 \cdot g_A(a) + \in, \quad (3)$$

where $g_S(\cdot)$ and $g_A(\cdot)$ are increasing functions with inverses $g_S^{-1}$ and $g_A^{-1}$, and $\in$ is a zero mean random variable with probability density function $f_S(\cdot)$. With this formulation it is assumed that neither of the functions $g_S(\cdot)$ and $g_A(\cdot)$ have parameters in need of estimation from the data. Estimates of $\beta_0$, $\beta_1$ and any additional parameters defining $f_S(\cdot)$ can be estimated from n data pairs $\{(a_i,s_i),i=1,\ldots,n\}$ of flaws sizes and signals by the maximum likelihood (ML) method. That is, let $\theta$ be the vector of parameters needed to fully specify the density $f_S(\cdot)$, then the ML estimates are given by $\hat{\beta}_0$, $\hat{\beta}_1$, and $\hat{\theta}$ which are the solutions to $$\max_{\beta_0,\beta_1,\theta} \prod_{i=1}^{n} \{f_S(g_S(s_i) - [\beta_0 + \beta_1 \cdot g_A(a)])\}$$

Letting $x = g_A(a)$ and $y = g_S(S)$ and $$f_S(x) = (\sqrt{2\pi})^{-1} e^{-\frac{x^2}{2}}$$

then equation (3) is the usual linear regression with Gaussian assumption for the errors given as $$y = \beta_0 + \beta_1 \cdot x + \in. \quad (4)$$

In this case the ML estimates and the least square linear regression give the same estimates.

Equation (4) is written as a function of the signal having a mean depending on the flaw size with probabilistic variation around that mean. In designing POD quantification experiments the flaw sizes may be set and signals measured corresponding to those individual flaws. It is thus appropriate for the error structure in the model to be associated with the signal measurement. However, once the relationship of signal to flaw size is estimated we can ask the inverse question of what is the best guess for the flaw size that corresponds to a measured signal not included in the original data set.

There are two general approaches to estimating the flaw size corresponding to a subsequently measured signal, s', following the "calibration" step. The classical approach is to simply solve the mean equation in terms of the flaw size. That is, set $$x' = \frac{y' - \hat{\beta}_0}{\hat{\beta}_1}.$$

This is equivalent to reading of the flaw value corresponding to a given signal from the mean line previously fitting the signal relationship to the flaw size. The second approach is to recast the problem as if the regression was for determining the flaw size while treating the signal as the independent variable. That is, find the coefficients for the regression $$x = \gamma_0 + \gamma_1 \cdot y + \in. \quad (5)$$

and then set $x' = \hat{\gamma}_0 + \hat{\gamma}_1 \cdot y' + \in$. It should be noted that these two approaches are not equivalent. That is $\hat{\gamma}_1 \neq 1/\hat{\beta}_1$, nor is $\hat{\gamma}_0 \neq \hat{\beta}_0/\hat{\beta}_1$.

We will follow the classical approach as it also provides the maximum likelihood estimate for the unknown flaw size in the Gaussian models. To see this we consider the set of n data pairs $\{(x_i,y_i),i=1,\ldots,n\}$ of flaws sizes and signals (or appropriate functions of them) as well as one additional signal $y_{n+1}$ $y_{n+1}$ for which the corresponding flaw size, $x_{n+1}$, is unknown. Using the regression model (4) and making the Gaussian assumption that $\in \approx N(0,\sigma^2)$ we write the likelihood function as $$L = \prod_{i=1}^{n+1} \frac{1}{\sqrt{2\pi\sigma^2}} \exp\left(-\frac{1}{2\sigma^2}(y_i - \beta_0 - \beta_1 \cdot x_i)^2\right)$$

Hence the log likelihood is given by $$LL(\beta_0, \beta_1, \sigma, x_{n+1}) = \quad (6)$$

$$-\frac{n+1}{2}\ln(2\pi) - (n+1)\ln(\sigma) - \frac{1}{2\sigma^2}\sum_{i=1}^{n+1}(y_i - \beta_0 - \beta_1 \cdot x_i)^2$$

The parameters that the log likelihood would be maximized over to give an MLE are shown in the argument list.

Initially we will treat $x_{n+1}$ as known, as in that case we know the maximum likelihood estimates for the other parameters. Specifically they are given in terms of the following statistics.

$$S_{xy} = \frac{1}{n+1} \cdot \sum_{i=1}^{n+1} (x_i - \overline{X}) \cdot (y_i - \overline{Y}),$$

$$S_x^2 = \frac{1}{n+1} \cdot \sum_{i=1}^{n+1} (x_i - \overline{X})^2,$$

$$\text{and } S_y^2 = \frac{1}{n+1} \cdot \sum_{i=1}^{n+1} (y_i - \overline{Y})^2$$

where $\overline{X}$ and $\overline{Y}$ are the means of the x and y data. We also write $$r = \frac{S_{xy}}{S_x \cdot S_y}.$$

It is well known that the maximum likelihood estimates are given by $$\hat{\beta}_1 = \frac{S_y}{S_x} \cdot r = \frac{S_{xy}}{S_x^2},$$

$$\hat{\beta}_0 = \overline{Y} - \hat{\beta}_1 \cdot \overline{X},$$

$$\text{and } \hat{\sigma}^2 = \frac{1}{n+1} \sum_{i=1}^{n+1} (y_i - \hat{\beta}_0 - \hat{\beta}_1 \cdot x_i)^2$$

Making the substitutions back into equation (6) we see that $$LL = -\frac{n+1}{2}\ln(2\pi) - (n+1)\ln(\hat{\sigma}) - \frac{n+1}{2}$$

and that the log likelihood is maximized when the estimated variance is minimized. Thus, assuming that $x_{n+1}$ is known we know that the parameter estimates that maximizes the likelihood also minimizes $\hat{\sigma}^2$. Note that $$\hat{\sigma}^2 = \frac{n}{n+1}\left(\frac{1}{n}\sum_{i=1}^{n}(y_i - \hat{\beta}_0 - \hat{\beta}_1 \cdot x_i)^2\right) + \frac{(y_{n+1} - \hat{\beta}_0 - \hat{\beta}_1 \cdot x_{n+1})^2}{n+1}$$

We know that the first term on the right hand side is minimized by setting $\hat{\beta}_0$ and $\hat{\beta}_1$ to the solutions based on the first n data points. The contribution of the $x_{n+1}$ term can be made 0 by letting $$\hat{x}_{n+1} = \frac{y_{n+1} - \hat{\beta}_0}{\hat{\beta}_1}.$$

Not done here, but with a little algebra it can be shown that the MLE estimates for the parameters based on the n+1 data pairs $$\left\{(x_i, y_i), i = 1, \ldots, n, \left(\frac{y_{n+1} - \hat{\beta}_0}{\hat{\beta}_1}, y_{n+1}\right)\right\}$$

are the same as those based on just the first n data pairs, where the flaw sizes are all known.

It should be noted that not only is the estimator for $x_{n+1}$ given by $$\frac{y_{n+1} - \hat{\beta}_0}{\hat{\beta}_2}$$

not unbiased, that in fact the distribution does not have a finite variance nor mean. Thus the usual method of confidence intervals using the estimated value plus or minus an appropriate multiple of the standard error cannot be applied. There are several approaches one can take to provide reasonable confidence limits for the unknown flaw size characteristic, $x_{n+1}$. One that we develop here is to write out the distribution theory for $y_{n+1}$ as if $x_{n+1}$ is known and $y_{n+1}$ is a random variable. Developing this theory we can write the confidence statement that holds for $y_{n+1}$ which is a function of $x_{n+1}$, but instead of constructing the interval for the signal we treat the signal as given and instead write the interval in terms of the $x_{n+1}$.

Here we give the results utilizing the following terms:

The percentile of the t distribution with n−2 degrees of freedom and upper tail probability of $\alpha/2$ given by $t_{\alpha/2; n-2}$ The mean of the signal data is $$\overline{Y} = \frac{1}{n}\sum_{i=1}^{n} y_i$$

The mean of the flaw data is $$\overline{X} = \frac{1}{n}\sum_{i=1}^{n} x_i$$

$$\hat{\beta}_1 = \frac{\sum_{i=1}^{n}(x_i - \overline{X}) \cdot (y_i - \overline{Y})}{\sum_{i=1}^{n}(x_i - \overline{X})^2}, \text{ and } \hat{\beta}_0 = \overline{Y} - \hat{\beta}_1 \cdot \overline{X}$$

$$\hat{\sigma}^2 = \frac{\sum_{i=1}^{n}(y_i - \hat{\beta}_0 - \hat{\beta}_1 \cdot x_i)^2}{n-2}$$

is the unbiased estimate for the variance and $$a = \hat{\beta}_1^2 - \frac{\hat{\sigma}^2 t_{\alpha/2; n-2}^2}{\sum_{i=1}^{n}(x_i - \overline{X})^2}$$

Using the above values determined from a "calibration" run the following procedure is used to estimate the flaw size from an unknown flaw size producing an observed signal of $y_{n+1}$ 1. Estimate of $x_{n+1}$ is given by $$\hat{x}_{n+1} = \frac{y_{n+1} - \hat{\beta}_0}{\hat{\beta}_1} = \overline{X} + \frac{y_{n+1} - \overline{Y}}{\hat{\beta}_1}$$

2. To obtain a 1−α1−α confidence limit for $x_{n+1}$ we have to assure that the 1−α confidence limit for $\beta_1$ does not include 0. Thus test the hypothesis, HO: $\beta_1 = 0$ versus the alternative, Ha: $\beta_1 \neq 0$ with a size α test. That is reject HO if and only if $$\frac{\hat{\beta}_1^2 \cdot \sum_{i=1}^{n}(x_i - \overline{X})^2}{\hat{\sigma}_2} \geq t_{\alpha/2;n-2}^2$$

3. If HO is not rejected then the confidence interval for $x_{n+1}$ would be infinite as there is not enough evidence that a dependency between signal and flaw size exists.

4. A rejection of the null hypothesis in step 2 assures the existence of a finite 100(1−α) % confidence interval for $x_{n+1}$ $$\text{Lower} = \overline{X} + \frac{\hat{\beta}_1(y_{n+1} - \overline{Y})}{a} - \frac{\hat{\sigma} \cdot t_{\alpha/2;n-2}}{a}\sqrt{a\left(\frac{n+1}{n}\right) + \frac{(y_{n+1} - \overline{Y})^2}{\sum_{i=1}^{n}(x_i - \overline{X})^2}}$$

and $$\text{Upper} = \overline{X} + \frac{\hat{\beta}_1(y_{n+1} - \overline{Y})}{a} + \frac{\hat{\sigma} \cdot t_{\alpha/2;n-2}}{a}\sqrt{a\left(\frac{n+1}{n}\right) + \frac{(y_{n+1} - \overline{Y})^2}{\sum_{i=1}^{n}(x_i - \overline{X})^2}}$$

The endpoints constituting the interval are not necessarily equidistant from the point estimate.

Having thus described several aspects of at least one embodiment of this invention, it is to be appreciated that various alterations, modifications, and improvements will readily occur to those skilled in the art.

Such alterations, modifications, and improvements are intended to be part of this disclosure, and are intended to be within the spirit and scope of the invention. Accordingly, the foregoing description and drawings are by way of example only.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer readable medium (or multiple computer readable media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

In this respect, it should be appreciated that one implementation of the above-described embodiments comprises at least one computer-readable medium encoded with a computer program (e.g., a plurality of instructions), which, when executed on a processor, performs some or all of the above-discussed functions of these embodiments. As used herein, the term "computer-readable medium" encompasses only a computer-readable medium that can be considered to be a machine or a manufacture (i.e., article of manufacture). A computer-readable medium may be, for example, a tangible medium on which computer-readable information may be encoded or stored, a storage medium on which computer-readable information may be encoded or stored, and/or a non-transitory medium on which computer-readable information may be encoded or stored. Other non-exhaustive examples of computer-readable media include a computer memory (e.g., a ROM, a RAM, a flash memory, or other type of computer memory), a magnetic disc or tape, an optical disc, and/or other types of computer-readable media that can be considered to be a machine or a manufacture.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Embodiments described herein are related to the Application filed concurrently herewith, Ser. No. 12/795,561 entitled "Component Adaptive Life Management," the entire disclosure of which is hereby incorporated herein by reference.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. An inspection system comprising:
   a sensor for collecting first spatial data from a component, the first spatial data comprising a first sensor response for at least one location on the component; and
   a computing system comprising:
      an inspection archive comprising second spatial data having a second sensor response for the component and third spatial data having a third sensor response for the component, wherein the first, second and third spatial data are a set of spatial data;
      a database comprising a plurality of data points, each data point storing a material condition of the component and a time;
      a filtering module to spatially register the set of spatial data;
      an estimation module to compute a first change in the material condition from the spatially registered set of spatial data, compute a second change in the material condition from the spatially registered set of spatial data, and estimate a current condition of the component based at least in part on the first change; and
      a prediction module to predict a future condition of the component, based at least in part on the current condition, using the database, wherein the future condition is further based on the second change.

2. The inspection system of claim 1, wherein said database is generated offline using a phenomenological model.

3. The inspection system of claim 1, wherein:
   the data points span a range of interest for each of the material condition and the time, and
   each database data point also includes values for at least two properties to be estimated, the values being generated using a model.

4. The inspection system of claim 3, wherein the material condition is crack size, the time is measured in equivalent cycles, and one of the two values estimated at each data point is remaining life.

5. The inspection system of claim 1, wherein the current condition is described by a probability density function, and wherein the prediction module generates a distribution function describing, probabilistically, the future condition of the component.

6. The inspection system of claim 5, wherein the prediction module predicts the future condition of the component at a next scheduled inspection time, and the computing system further comprises:
   a decision module that determines whether the future condition predicted at the next scheduled inspection time has a risk of failure that exceeds a damage tolerance limit.

7. The inspection system of claim 6, wherein if the decision module determines that the risk of failure at the next scheduled inspection exceeds the damage tolerance threshold limit, and in response provides an instruction to replace or repair the component.

8. The inspection system of claim 6, wherein if the decision module determines that the risk of failure at the next scheduled inspection exceeds the damage tolerance limit, then in response the decision module reschedules the next inspection time to an earlier time.

9. A non-transitory computer-readable storage medium comprising computer-executable instructions that, when executed by at least one processor, perform a method comprising acts of:
   receiving at least three sets of sensor data, each of the at least three sets of sensor data comprising spatial data for a measured material condition of a component;
   spatially registering the at least three sets of sensor data with respect to each other and the component;
   computing a first change in the material condition of the component from the spatially registered at least three sets of sensor data;
   estimating the current condition based at least in part on the first change in the material condition;
   computing a second change in the material condition using the at least three sets of sensor data; and predicting a future condition of the component at a future time based at least in part on the estimated current condition, wherein predicting the future condition is further based on the second change.

10. The non-transitory computer-readable storage medium of claim 9, wherein the future condition of the component is predicted using a database comprising a plurality of precomputed material conditions of the component, each precomputed material condition computed for a respective operating condition and time.

11. The non-transitory computer-readable storage medium of claim 10, wherein predicting the future condition comprises interpolating the future condition at the future time from the precomputed material conditions in the database.

12. The non-transitory computer-readable storage medium of claim 9, wherein predicting the future condition of the component comprises determining a distribution function describing, probabilistically, the future condition of the component at the future time.

13. The non-transitory computer-readable storage medium of claim 9, wherein the future time at which the future condition of the component is predicted is a next scheduled inspection time.

14. The non-transitory computer-readable storage medium of claim 13, wherein the method further comprises determining whether the future condition predicted at the next scheduled inspection time has a probability above a threshold that said future condition may exceed a damage tolerance limit and, if so, providing an instruction to replace or repair the component or to reschedule the next inspection time to an earlier time.

15. The non-transitory computer-readable storage medium of claim 9, wherein predicting the future condition comprises determining the future time as a time at which the future condition meets a replacement condition for the component.

16. The non-transitory computer-readable storage medium of claim 15, wherein the future time is measured in equivalent fatigue cycles.

17. The non-transitory computer-readable storage medium of claim 15, wherein the future condition is a predefined crack size limit.

18. The non-transitory computer-readable storage medium of claim 9, wherein the method further comprises an act of predicting a probability distribution for a future condition of the component using a probability distribution function for the current condition and a hyperlattice generated using a progression model for a process.

19. The non-transitory computer-readable storage medium of claim 18, wherein the process is crack initiation and growth.

20. The non-transitory computer-readable storage medium of claim 18, wherein the process is the evolution of a medical condition.

21. The non-transitory computer-readable storage medium of claim 18, wherein the process is a manufacturing process.

22. The non-transitory computer-readable storage medium of claim 18, wherein the process is a motion of a device.

23. The non-transitory computer-readable storage medium of claim 18, wherein the process is a machining process.

* * * * *